(12) United States Patent
Himmelreich et al.

(10) Patent No.: US 8,624,020 B2
(45) Date of Patent: Jan. 7, 2014

(54) METHOD FOR ISOLATING AND PURIFYING NUCLEIC ACIDS

(75) Inventors: Ralf Himmelreich, Langendfeld (DE); Sabine Werner, Duesseldorf (DE)

(73) Assignee: Qiagen GmbH, Hilden (DE)

( * ) Notice: Subject to any disclaimer, the term of this patent is extended or adjusted under 35 U.S.C. 154(b) by 74 days.

(21) Appl. No.: 13/061,928

(22) PCT Filed: Sep. 2, 2009

(86) PCT No.: PCT/EP2009/061358
§ 371 (c)(1),
(2), (4) Date: Mar. 29, 2011

(87) PCT Pub. No.: WO2010/026167
PCT Pub. Date: Mar. 11, 2010

(65) Prior Publication Data
US 2011/0224419 A1    Sep. 15, 2011

(30) Foreign Application Priority Data
Sep. 3, 2008    (EP) ..................... 08163624

(51) Int. Cl.
*C07H 21/00*    (2006.01)
(52) U.S. Cl.
USPC .................. 536/25.4; 536/25.41; 536/25.42
(58) Field of Classification Search
None
See application file for complete search history.

(56) References Cited

U.S. PATENT DOCUMENTS

| | | | |
|---|---|---|---|
| 5,610,287 A | 3/1997 | Nikiforov et al. | |
| 5,705,628 A | 1/1998 | Hawkins | |
| 7,241,572 B2 * | 7/2007 | Kojima et al. | 435/6.16 |
| 8,247,545 B1 | 8/2012 | Colpan | |
| 2004/0167324 A1 | 8/2004 | Kojima et al. | |
| 2005/0079535 A1 | 4/2005 | Kirchgesser et al. | |
| 2006/0160085 A1 | 7/2006 | Hillebrand et al. | |

FOREIGN PATENT DOCUMENTS

| | | |
|---|---|---|
| DE | 10253351 | 5/2002 |
| JP | 2000186136 | 7/2000 |
| JP | 2000297051 | 10/2000 |
| WO | 2004042058 | 5/2004 |

OTHER PUBLICATIONS

Vogelstein et al., "Preparative and Analytical Purification of DNA from Agarose," Proc. Nat. Acad. Sciences, USA, 76(2), 615-619 (Feb. 1979).*
Boom et al., "Rapid and Simple Method for Purification of Nucleic Acids," Journal of Clinical Microbiology, 28(3), 495-503 (Mar. 1990).*
International Search Report and Written Opinion (German Language—18 pages) of PCT/EP2009/061358 mail dated Nov. 3, 2009.
Qiagen GmbH, BIOSPRINT 96 DNA Handbook (Mar. 2006).
Qiagen GmbH, EZ1 DNA Blood Handbook (Apr. 2010).
Qiagen GmbH, QIAAMP 96 DNA Blood Handbook (Apr. 2010).
Qiagen GmbH, DNEASY Blood and Tissue Handbook (Jul. 2006).
Qiagen GmbH, RNEASY 96 Blood and Tissue Handbook (Jan. 2002).
Qiagen GmbH, QIAquick Multiwell PCR Purification (Sep. 2003).
NCBI PubChem Substance Database, Deposit Substance ID 24866409, Version 2, Deposit Date Jul. 12, 2007; Modify Date, Apr. 7, 2009, available at http://pubchem.ncbi.nlm.nih.gov/summary/summary.cgi?sid=24866409&version=2 (last accessed Jan. 16, 2013).
NCBI PubChem Substance Database, Deposit Substance ID 24866411, Version 3; Deposit Date Jul. 12, 2007; Modify Date, May 14, 2009, available at http://pubchem.ncbi.nlm.nih.gov/summary/summary.cgi?sid=24866411 (last accessed Jan. 16, 2013).

* cited by examiner

*Primary Examiner* — Lawrence E Crane
(74) *Attorney, Agent, or Firm* — Baker, Donelson, Bearman, Caldwell & Berkowitz PC

(57) ABSTRACT

The present invention relates to a method for the isolation and purification of nucleic acids by elution of nucleic acids from nucleic acid-containing samples, and biological materials, using a wash buffer comprising an alcohol having 1 to 3 carbon atoms and at least one further solvent selected from the group consisting of alkane diols and alkane triols having 2 to 6 carbon atoms, monocarboxylic acid esters and dicarboxylic acid diesters having 2 to 6 carbon atoms in the acidic component and 1 to 4 carbon atoms in the alcoholic component; (poly)ethylene glycols and ether derivatives and ester derivatives thereof, and poly(4-styrene sulfonic acid-co-maleic acid) sodium salt solution. The present invention further relates to a kit for carrying out the method of the invention.

19 Claims, 14 Drawing Sheets

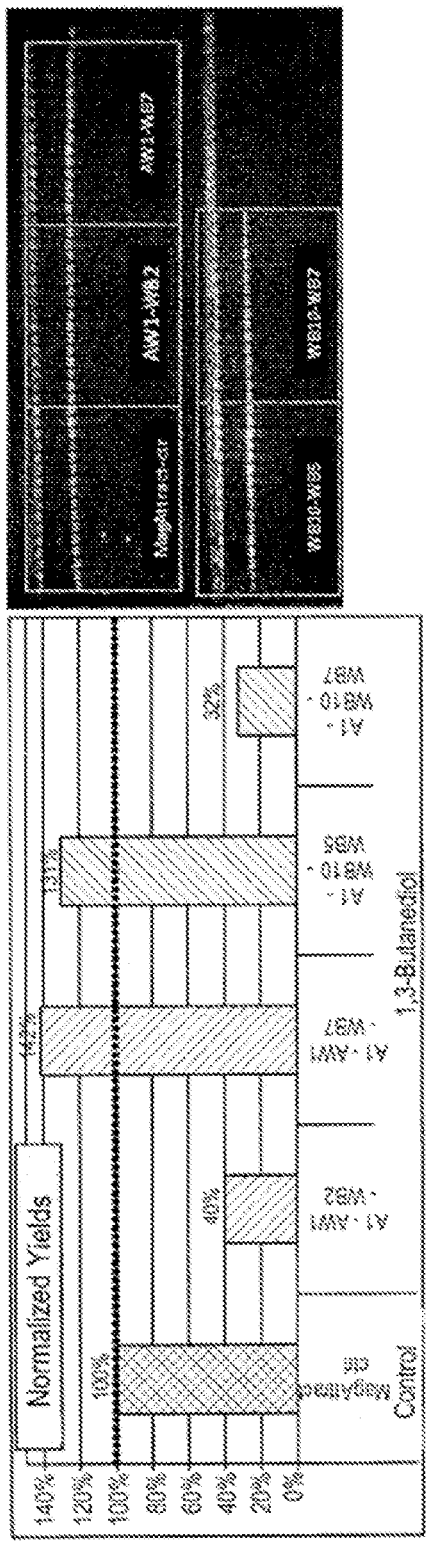
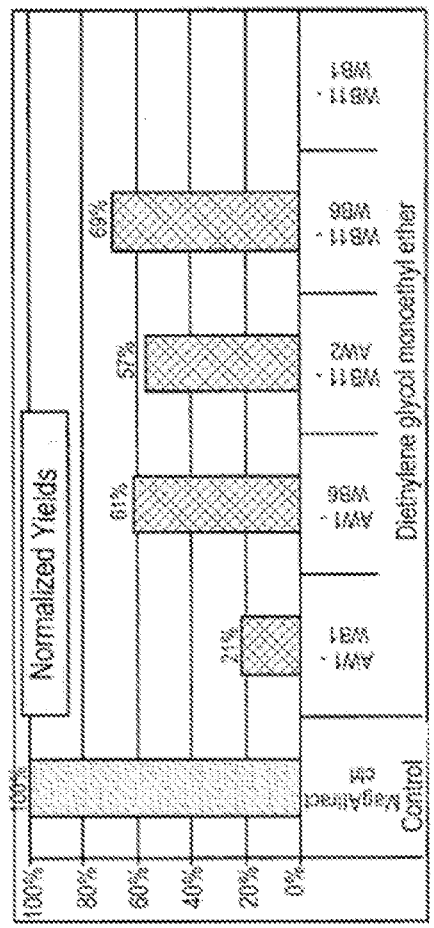
Fig. 5A
Fig. 5B

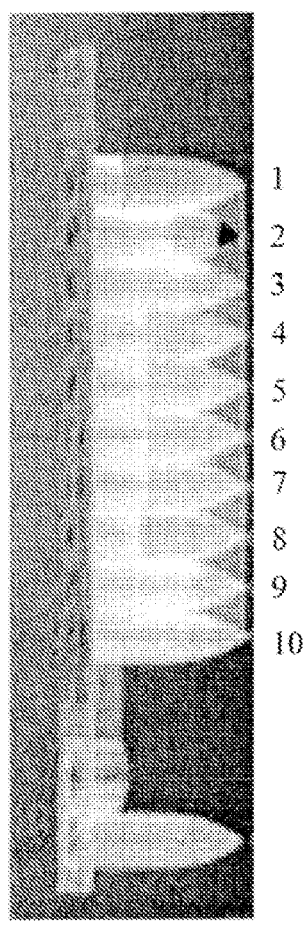 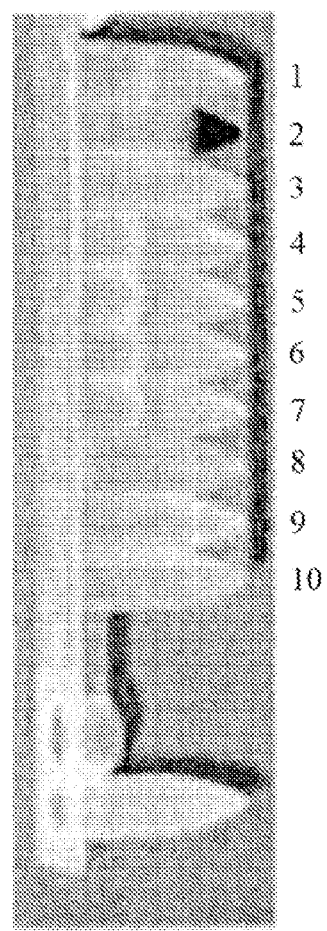
Fig. 22A                               Fig. 22B

METHOD FOR ISOLATING AND PURIFYING NUCLEIC ACIDS

CROSS REFERENCE TO RELATED APPLICATIONS

This application is a §371 National Stage Application of PCT/EP2009/061358 filed Sep. 2, 2009, which claims priority to EP 08163624.3 filed Sep. 3, 2008.

BACKGROUND OF THE INVENTION

1. Field of the Invention

The present invention relates to a method for the isolation and purification of nucleic acids by separation of the nucleic acids from nucleic acid-containing samples, and biological materials. Furthermore, the present invention relates to a kit for carrying out the method of the present invention.

2. Description of Related Art

A method for the isolation and purification of nucleic acids, already known in the prior art, is based on the adsorption of nucleic acids on glass or silica particles in the presence of chaotropic salts, and the subsequent recovery of the adsorbed nucleic acids (Vogelstein, B. and Gillespie, D. (1979); "Preparative and analytical purification of DNA from Agarose", Proc. Natl. Acad. Sci. USA 76: 615-619). According to this method, DNA is isolated and purified over agarose using high concentrations of chaotropic salts, such as sodium iodide, sodium perchlorate or guanidinium thiocyanate. The RNA or DNA may also be isolated or purified from various mixtures (Boom, R., 1990; "Rapid and simple method for purification of nucleic acids", J. Clin. Microbiol. 28: 495-503).

After completion of the nucleic acid purification, nucleic acids are often used in polymerase chain reaction (PCR). The PCR amplifies nucleic acids in a sequence-specific manner and is therefore widely used in genetic diagnosis or DNA diagnosis. The use of PCR technology in the clinical routine involves several problems. It is known that inhibitory substances that have not been removed from the nucleic acid purification step may inhibit PCR. Such inhibitory substances are, e.g., hemoglobin and surfactants, which were used in the nucleic acid extraction process. In light of the above it is apparent that the methods for the extraction and purification of nucleic acids are very important and relevant (Oshima et al., JJCL A, 22(2) 145-150 (1997)).

Methods for the extraction and purification of nucleic acids are frequently automated. In the prior art there already exist automated nucleic acid extraction methods, as described, e.g., in JP-A-107854/1999 and in JP-A-266864/1999. In most methods for the isolation and purification of nucleic acids, a solution containing a high concentration of salts and a high concentration of alcohol, and in which the nucleic acids are present, is brought into contact with an adsorption surface. The adsorption surface may be in the form of a resin in a column. Then the nucleic acids are adsorbed on this surface and later eluted by means of solutions containing less concentrated salt solutions.

The problem with most methods for the isolation and purification of nucleic acids consists in that the yield of nucleic acids is comparatively small. A further problem is that, according to the IATA (International Air Transportation Association) Regulations, ethanol-containing solutions are classified as dangerous materials (HAZMAT; hazardous materials). According to the IATA Regulations, all products, materials and goods are categorized in nine main classes. In view of the classification as dangerous goods, additional fees and taxes become due for air transport. It was therefore the object of the present invention to replace as far as possible ethanol (or isopropanol) in the method for the purification and extraction of nucleic acids to facilitate the isolation and purification of nucleic acids, to provide an ethanol-free method and to facilitate the transport of air cargo.

From the prior art are known substitutes for alcohol in methods for the purification of nucleic acids, which, however, solve the above discussed problems only in part (US 2004/0167324). The majority of the substances described therein either fall under the HAZMAT IATA Regulations or have an acrid smell which absolutely requires preparation in a fume hood.

SUMMARY OF THE INVENTION

Surprisingly, in connection with the present invention solvents were found for wash buffers for washing nucleic acids immobilized on surfaces, which make it possible that the wash buffer is substantially free of alcohol, i.e. ethanol.

The present invention, thus, relates to a method for washing nucleic acids which are immobilized on surfaces, wherein nucleic acids immobilized on surfaces are brought into contact with a wash buffer and the wash buffer is substantially free of ethanol.

BRIEF DESCRIPTION OF THE DRAWINGS

FIGS. 1-21 depict various embodiments of the present invention.

DETAILED DESCRIPTION OF A PREFERRED EMBODIMENT

Figure 1:
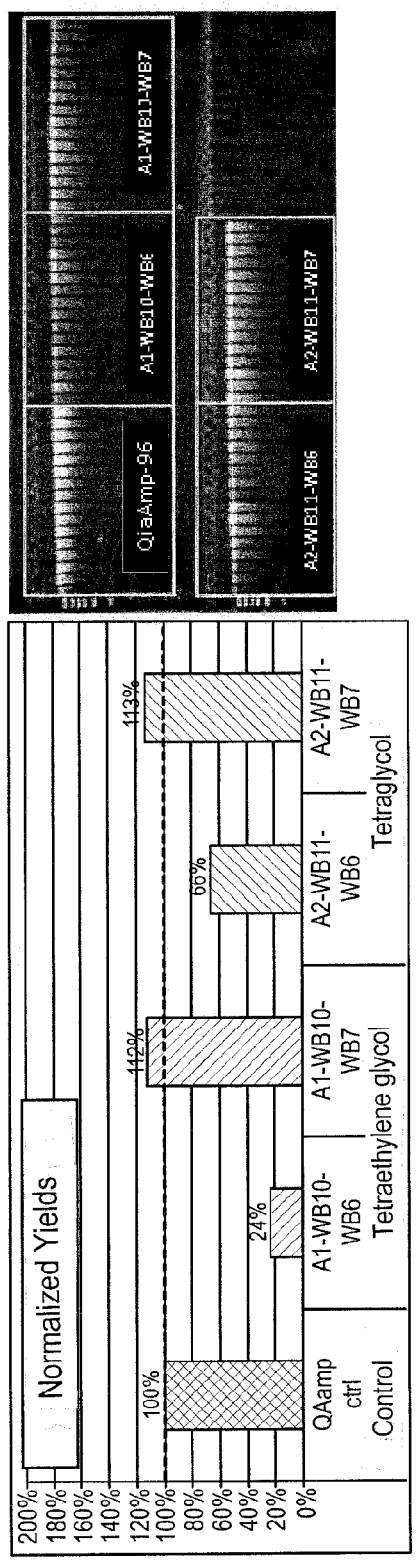

In accordance with the present invention, "substantially free of ethanol" means that ethanol is present in the wash buffer in a concentration of less than 24% by volume, preferably of less than 16% by volume, and most preferably not present at all.

The present invention relates, in particular, to a method for washing nucleic acids immobilized on surfaces, wherein the wash buffer comprises solvents selected from the group consisting of C3 to C5 alkyldioles, as well as short-chain ethylene glycol derivatives and diverse water-soluble polymeric compounds, and wherein the wash buffer is substantially free of ethanol.

In a preferred embodiment, the present invention relates to a method for washing nucleic acids immoblized on surfaces, wherein the wash buffer comprises solvents selected from the group consisting of 1,2-butanediol, 1,2-propanediol, 1,3-butanediol, 1-methoxy-2-propanol-acetate, 3-methyl-1,3,5-pentanetriol, DBE-2 dibasic ester, DBE-3 dibasic ester, DBE-4 dibasic ester, DBE-5 dibasic ester, DBE-6 dimethyl adipate, diethylene glycol monoethyl ether (DGME), diethylene glycol monoethyl ether acetate (DGMEA), ethyl lactate, ethylene glycol, poly(2-ethyl-2-oxazoline), poly(4-styrene sulfonic acid-co-maleic acid) sodium salt solution, tetraethylene glycol (TEG), tetraglycol (tetrahydrofurfuryl-polyethylene glycol ether), tetrahydrofurfuryl-polyethylene glycol 200, tri(ethylene glycol)-divinyl ether, anhydrous triethylene glycol, triethylene glycol monoethyl ether.

Particularly preferably, the wash buffer is selected from the group consisting of tetraglycol, tetraethylene glycol, 1,3-butanediol, 1,2-butanediol and diethylene glycol monoethyl ether.

Furthermore, the present invention relates to a method for extracting nucleic acids from a solution, comprising the steps of:

(a) adding a binding mediator to the nucleic-acid containing solution,
(b) contacting the solution containing the binding mediator and the nucleic acids with a surface under chaotropic and/or high-salt conditions,
(c) binding or adsorption of the nucleic acids on the surface,
(d) washing the surface according to the method of the invention for washing nucleic acids immobilized on surfaces,
(e) recovery of the nucleic acids bound to or adsorbed on the surface by elution.

Chaotropic conditions are obtained by the addition of chaotropic substances. Those chemical substances are called chaotropic which disrupt ordered hydrogen bonds in aqueous solutions. They thus reduce the hydrophobic effect and have a denaturating effect on proteins, since the clustering of hydrophobic amino acids in water is the main reason for protein folding. Examples for chaotropic substances are barium salts, guanidinium hydrochloride, thiocyanates, such as guanidinium thiocyanate, perchlorate or even sodium chloride. According to their solubility product, chaotropic salts may be used in concentration ranges of between 1 M and 8 M.

High-salt conditions means highly concentrated salt solutions, wherein the salt concentration in the solution is at least 1 M, preferably 1-4 M.

However, it is also possible to take alternative measures to chaotropic or high-salt conditions, which achieve the same effect, i.e. binding of the nucleic acids to be purified to the surface.

Preferably, the binding mediator is selected from the group consisting of diethylene glycol monoethyl ether, diethylene glycol monoethyl ether acetate, furfuryl alcohol, poly(1-vinylpyrrolidon-co-2-dimethyl-aminoethyl-methacrylate), poly(2-ethyl-2-oxazoline), poly(4-ammonium-styrene-sulfonic acid), tetraethylene glycol dimethyl ether, tetraethylene glycol, tetrahydrofurfuryl-polyethylene glycol 200 and triethylene glycol monoethyl ether.

The person skilled in the art can successfully substitute ethanol in the binding process during nucleic acid preparation by mixtures of the mentioned binding mediators. Since ethanol-containing solutions of up to 24% (vol/vol) are not classed as HAZMAT, it is also possible to use mixtures of the binding mediators with ethanol.

Preferably, the binding mediators are present in the following concentrations:
diethylene glycol monoethyl ether (DGME) [CAS 111-90-0]—concentration range 70-99% by volume, preferred concentration 99.0%; in combination with ethanol: 60-80% by volume DGME and 16-24% by volume ethanol
diethylene glycol monoethyl ether acetate (DGMEA) [CAS 112-15-]—concentration range 70-99% by volume, preferred concentration 99.0% by volume, in combination with ethanol: 60-80% by volume DGMEA and 16-24% by volume ethanol
furfuryl alcohol [CAS 98-00-]—concentration range 20-30% by volume, preferred concentration 30% by volume
poly(1-vinylpyrrolidone-co-2-dimethyl-aminoethyl-methacrylate) [CAS 30581-59-0)—concentration range 3-5% by volume, preferred concentration 5% by volume
poly(2-ethyl-2-oxazolin) [CAS 25805-17-]—concentration range 9-15% by volume (w/v), preferred concentration 12% by volume; in combination with ethanol: 22.5% by volume (w/v) and 16-24% by volume (v/v) ethanol
poly(4-ammoniumstyrene sulfonic acid) [CAS 29965-34-]—concentration range 8-22% by volume (w/v), preferred concentration 12% by volume; in combination with ethanol: 8-22 (w/v) and 24% by volume (v/v) ethanol
tetraethylene glycol dimethylether [CAS 143-24-]—concentration range 70-98% by volume, preferred concentration 98% by volume; in combination with ethanol: 73.5% by volume and 24% by volume ethanol
tetraglycol (tetrahydrofurfuryl polyethylene glycol ether) [CAS 9004-76-]—preferred concentration with ethanol: 75% by volume and 16-24% by volume ethanol
tetrahydrofurfuryl polyethylene glycol 200 [CAS 31692-85-0]—concentration range 70-100% by volume, preferred concentration 100% by volume
triethylene glycol monoethyl ether [CAS 112-50-5]—concentration range 70-90% by volume, preferred concentration 90% by volume Elution buffers are generally buffered low-salt solutions with neutral to slightly alkaline pH value (e.g., buffer TE 10 mM Tris/Cl pH 8, 1 mM EDTA). The skilled person sometimes also uses distilled water.

In a particularly preferred variant of the method of the invention, the wash buffer is tetraglycol in a concentration of between 45% by volume to 80% by volume, preferably 52% by volume to 72% by volume; in the presence of 2 to 4 M, preferably 2.5 M of a chaotrope, such as guanidium hydrochloride, the preferred concentration of tetraglycol is between 45 to 55% by volume, preferably 50% by volume.

In another, particularly preferred variant of the method of the invention, the wash buffer is tetraethylene glycol in a concentration of 45 to 80% by volume, preferably of 50% by volume to 70% by volume. In the presence of 2 to 4 M, preferably 2.5 M of a chaotrope, such as guanidinium hydrochloride, the preferred concentration of tetraethylene glycol is 45 to 55% by volume, preferably 50% by volume.

In another, particularly preferred variant of the method of the invention, the wash buffer is 1,3-butanediol in a concentration from 45 to 85% by volume, preferably from 51% by volume to 80% by volume. In the presence of 2 to 4 M, preferably 2.5 M of a chaotrope, such as guanidinium hydrochloride, the preferred concentration of 1,3-butanediol is 45 to 55% by volume, preferably 49% by volume.

In another, particularly preferred variant of the method of the invention, the wash buffer is 1,2-butanediol in a concentration of 41% by volume to 71% by volume. In the presence of 2 to 4 M, preferably of 2.5 M of a chaotrope, such as guanidinium hydrochloride, the preferred concentration of 1,2-butanediol is 41 to 55% by volume, preferably 49% by volume.

In another, particularly preferred variant of the method of the invention, the wash buffer is in a concentration of 38 to 98% by volume, preferably of 60% by volume to 98% by volume. In the presence of 2 to 4 M, preferably of 2.5 M of a chaotropic agent, such as guanidinium hydrochloride, the preferred concentration of 1,2-butanediol is from 38 to 45% by volume, preferably 42% by volume.

The surfaces on which the nucleic acids are adsorbed can be based on materials selected from the following group: silica materials, carboxylated surfaces, zeolites and titanium dioxide.

In the method of the invention for the extraction of nucleic acids from a solution, the chaotropic and/or high-salt conditions of reaction step b) are preferably obtained by the addition of chaotropic salts, such as potassium iodide, guanidinium hydrochloride, guanidinium thiocyanate or sodium chloride, to the nucleic acid-containing solution.

The nucleic acid can be DNA, such as genomic DNA. The nucleic acid may also be RNA, such as total RNA. The nucleic acid can be single-stranded or double-stranded nucleic acid, such as short double-stranded DNA fragments.

The nucleic acid-containing solution can be obtained by lysis from a nucleic-acid containing material.

The nucleic-acid containing material can be selected from the group consisting of blood, tissue, smear preparations, bacteria cultures, urine, cell suspensions and adherent cells, PCR reaction mixtures and in vitro nucleic acid modification reaction mixtures. The nucleic acid-containing material may comprise human, animal or plant material.

The nucleic acid-containing solution can be obtained from a biochemical nucleic acid modification reaction.

Preferably, surfactants are added to the nucleic acid-containing solution. These surfactants are preferably used in concentration ranges from 0.1% by volume to 10% by volume. In addition, agents preventing foam formation (antifoams) may be added, preferable in a range from 0.01 to 1% by weight.

The present invention further relates to a reagent kit for washing nucleic acids immobilized on surfaces, comprising a solution 1 comprising a wash buffer which is substantially free of ethanol.

The present invention particularly relates to a reagent kit for washing nucleic acids immobilized on surfaces, comprising
  a solution 1 comprising the wash buffer selected from the group consisting of C3 and C4 alkyldioles, as well as short-chain ethylene glycol derivates and diverse water-soluble polymeric compounds, and wherein the wash buffer is substantially free of ethanol.

In a preferred embodiment of the reagent kit for washing nucleic acids immobilized on surfaces, the reagent kit comprises
  a solution 1 comprising the wash buffer selected from the group consisting of 1,2-butanediol, 1,2-propanediol, 1,3-butanediol, 1-methoxy-2-propanolacetate, 3-methyl-1,3,5-pentanetriol, DBE-2 dibasic ester, DBE-3 dibasic ester, DBE-4 dibasic ester, DBE-5 dibasic ester, DBE-6 dimethyl adipate, diethylene glycol monoethyl ether (DGME), diethylene glycol monoethyl ether acetate (DGMEA), ethyl lactate, ethylene glycol, poly(2-ethyl-2-oxazoline), poly(4-styrene sulfonic acid-co-maleic acid) sodium salt solution, tetraethylene glycol (TEG), tetraglycol (tetrahydrofurfuryl polyethylene glycol ether), tetrahydrofurfuryl polyethylene glycol 200, tri(ethylene glycol) divinyl ether, anhydrous triethylene glycol, triethylene glycol monoethyl ether.

In a particularly preferred embodiment of the reagent kit for washing nucleic acids immobilized on surfaces, the reagent kit comprises
  a solution 1 comprising the wash buffer selected from the group consisting of tetraglycol, tetraethylene glycol, 1,3-butanediol, 1,2-butanediol and diethylene glycol monoethyl ether.

The present invention further relates to a reagent kit for extracting nucleic acids from a solution, comprising the above mentioned reagent kit and additionally comprising
  a mixture 2 comprising binding mediator, and
  a mixture 3 comprising an eluant.

The binding mediator is preferably selected from the group consisting of diethylene glycol monoethyl ether, diethylene glycol monoethyl ether acetate, furfuryl alcohol, poly(l-vinylpyrrolidone-co-2-dimethyl-aminoethyl-methacrylate), poly(2-ethyl-2-oxazoline), poly(4-ammonium-styrene-sulfonic acid), tetraethylene glycol dimethyl ether, tetraethylene glycol, tetrahydrofurfuryl polyethylene glycol 200 and triethylene glycol monoethyl ether.

The person skilled in the art may also successfully replace ethanol in the binding process of the nucleic acid preparation by mixtures of the mentioned binding mediators. Since ethanol-containing solutions of up to 24% (vol/vol) are not classified as HAZMAT, it is also possible to use combinations of binding mediators with ethanol.

The binding mediators are preferably used in the following concentrations:
  diethylene glycol monoethyl ether (DGME) [CAS 111-90-0]—concentration range 70-99% by volume, preferred concentration 99.0% by volume; in combination with ethanol: DGME 60-80% by volume and ethanol 16-24% by volume
  diethylene glycol monoethyl ether acetate (DGMEA) [CAS 112-15-]—concentration range 70-99% by volume, preferred concentration 99.0% by volume; in combination with ethanol: DGMEA 60-80% by volume and ethanol 16-24% by volume
  furfuryl alcohol [CAS 98-00-]—concentration range 20-30% by volume, preferred concentration 30% by volume
  poly(1-vinyl-pyrrolidone-co-2-dimethyl-aminoethyl-methacrylate) [CAS 30581-59-0]—concentration range 3-5% by volume, preferred concentration 5% by volume
  poly(2-ethyl-2-oxazoline) [CAS 25805-17-]—concentration range 9-15% by volume (w/v), preferred concentration 12% by volume; in combination with ethanol: 22.5% by volume (w/v) and ethanol 16-24% by volume (v/v)
  poly(4-ammonium styrene sulfonic acid) [CAS 29965-34-]—concentration range 8-22% by volume (w/v), preferred concentration 12% by volume; in combination with ethanol: 8-22 (w/v) and ethanol 24% by volume (v/v)
  tetraethylene glycol dimethyl ether [CAS 143-24-]—concentration range 70-98% by volume, preferred concentration 98% by volume; in combination with ethanol: 73.5% by volume and ethanol 24% by volume
  tetraglycol [CAS 9004-76-]—preferred concentration with ethanol: 75% by volume and ethanol 16-24% by volume
  tetrahydrofurfuryl polyethylene glycol 200 [CAS 31692-85-0]—concentration range 70-100% by volume, preferred concentration 100% by volume
  triethylene glycol monoethyl ether [CAS 112-50-5]—concentration range 70-90% by volume, preferred concentration 90% by volume Generally, elution buffers are buffered low-salt solutions having a neutral to slightly alkaline pH value (e.g., buffer TE of the company QIAGEN GmbH, Hilden). The skilled person sometimes also uses distilled water.

The present invention further relates to a reagent kit for extracting nucleic acids from a solution, comprising the above mentioned reagent kit and a further solution 4 comprising a lysis buffer and a protease.

As already stated above, in the method of the invention for extracting nucleic acids from a solution, the chaotropic and/or high-salt conditions of reaction step b) are preferably obtained by the addition of chaotropic salts, such as potassium iodide, guanidinium hydrochloride, guanidinium thiocyanate or sodium chloride, to the nucleic acid-containing solution. Therefore, the present invention also relates to a reagent kit of the invention for extracting nucleic acids from a solution, wherein one of the solutions contains a chaotropic salt or has high-salt conditions.

The chaotropic salt is preferably selected from a group consisting of potassium iodide, guanidinium hydrochloride, guanidinium thiocyanate and sodium chloride.

The present invention also relates to the use of a reagent kit of the invention for the extraction of nucleic acids from biological materials, such as blood, tissue, smear preparations, bacteria, cell suspensions and adherent cells.

The present invention also relates to the use of a reagent kit of the invention for the purification of nucleic acids from biochemical reaction mixtures, PCR reaction mixtures and in vitro nucleic acid modification reaction mixtures.

Unless otherwise stated, the products, buffers and protocols (process instructions) described in the present application are published documents and commercially available products of the company QIAGEN GmbH, Hilden, Germany.

DESCRIPTION OF THE FIGURES

FIG. 1:
Behavior of tetraethylene glycol and tetraglycol, used in the QIAamp® 96 Spin Blood Protocol Left: normalized yields, determined by β-actin qPCR; right: agarose gel with the various samples
  A1: tetraethylene glycol
  First wash buffer: WB10: 48.5% by volume tetraethylene glycol; 2.5 M GuHCl
  Second wash buffer: WB6: 69.8% by volume tetraethylene glycol; 100 mM NaCl; 10 mM Tris-Cl pH 7.5
  Second wash buffer: WB7: 50.4% by volume tetraethylene glycol; 100 mM NaCl; 10 mM Tris-Cl pH 7.5
  A2: tetraglycol
  First wash buffer: WB 11: 50.0% by volume tetraglycol; 2.5 M GuHCl
  Second wash buffer: WB6: 72.0% by volume tetraglycol; 100 mM NaCl; 10 mM Tris-Cl pH 7.5
  Second wash buffer: WB7: 52.0% by volume tetraglycol; 100 mM NaCl; 10 mM Tris-Cl pH 7.5

Figure 2:
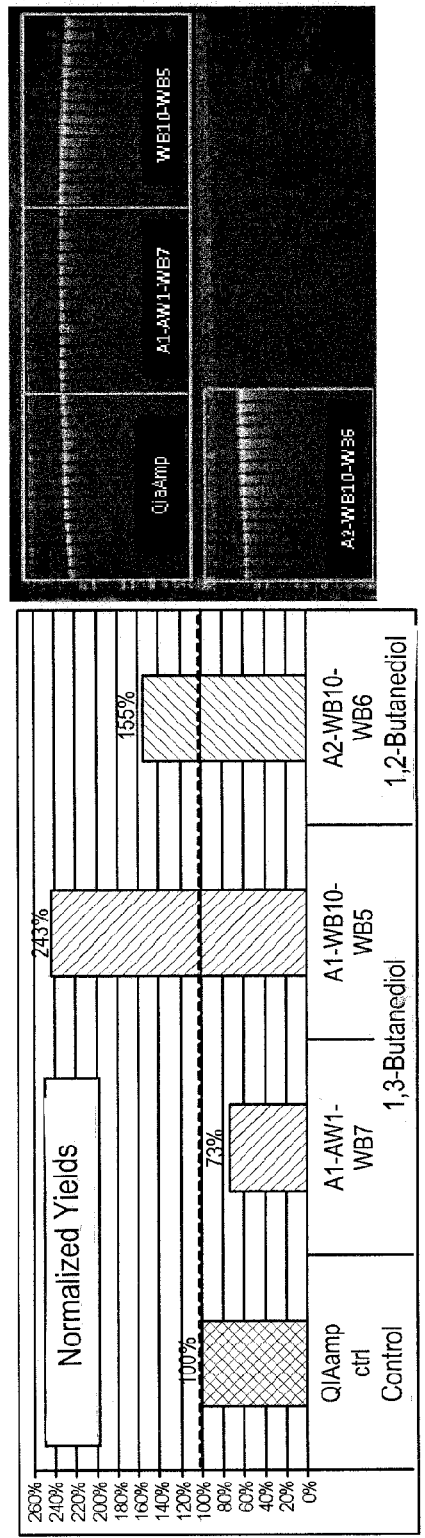

FIG. 2:
Behavior of 1,3-butanediol and 1,2-butanediol, used in the QIAamp® 96 Spin Blood Protocol Left: normalized yields, determined by β-actin qPCR; right: agarose gel with the various samples
  A1: 1,3-butanediol
  First wash buffer: WB10: 49.0% by volume 1,3-butanediol; 2.5 M GuHCl
  Second wash buffer: WB5: 80.0% by volume 1,3-butanediol; 100 mM NaCl; 10 mM Tris-Cl pH 7.5
  Second wash buffer: WB7: 51.0% by volume 1,3-butanediol; 100 mM NaCl; 10 mM Tris-Cl pH 7.5
  A2: 1,2-butanediol
  First wash buffer: WB10: 49.0% by volume 1,2-butanediol; 2.5 M GuHCl
  Second wash buffer: WB6: 71.0% by volume 1,2-butanediol; 100 mM NaCl; 10 mM Tris-Cl pH 7.5

Figure 3:
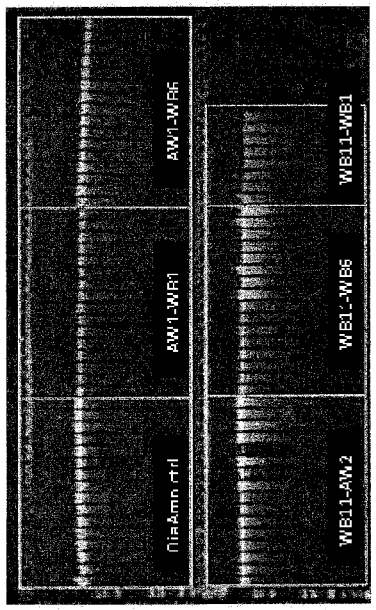
Figure 3:
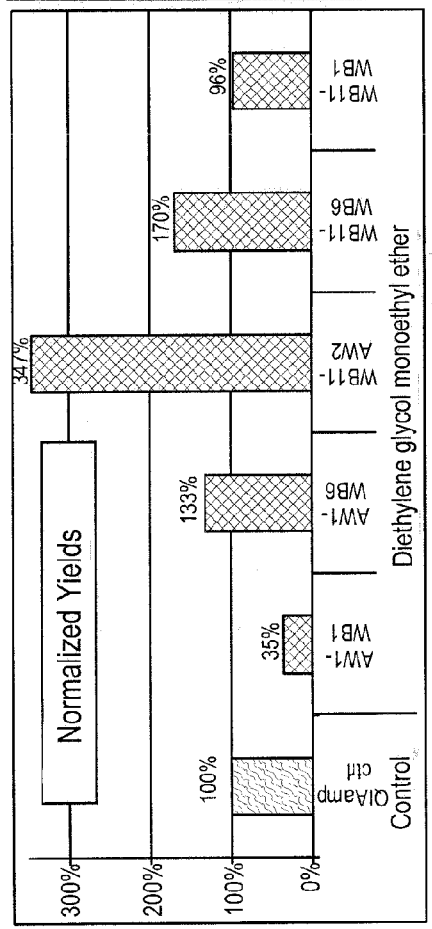

FIG. 3:
Behavior of diethylene glycol monoethyl ether, used in the QIAamp® 96 Spin Blood Protocol
Left: normalized yields, determined by β-actin qPCR; right: agarose gel with the various samples
  First wash buffer: QIAGEN Buffer AW1
  First wash buffer: WB11: 42% by volume diethylene glycol monoethyl ether; 2.5 M GuHCl
  Second wash buffer: WB 1. 98% by volume diethylene glycol monoethyl ether
  Second wash buffer: WB6: 71% by volume diethylene glycol monoethyl ether; 100 mM NaCl; 10 mM Tris-Cl pH 7.5

Figure 4:
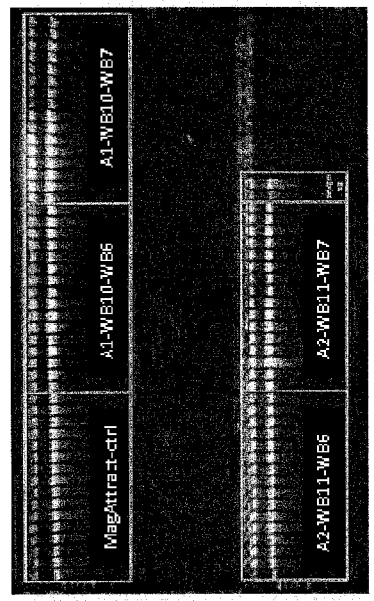
Figure 4:
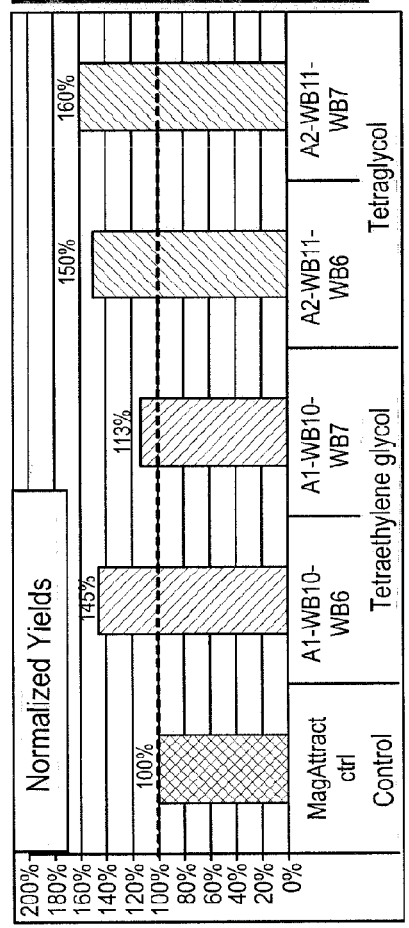

FIG. 4:
Behavior of tetraethylene glycol and tetraglycol, used in the BioSprint® 96 DNA Blood Protocol
Left: normalized yields, determined by β-actin qPCR; right: agarose gel with the various samples
  A1: tetraethylene glycol
  First wash buffer: WB10: 48.5% by volume tetraethylene glycol; 2.5 M GuHCl
  Second wash buffer: WB6: 69.8% by volume tetraethylene glycol; 100 mM NaCl; 10 mM Tris-Cl pH 7.5
  Second wash buffer: WB7: 50.4% by volume tetraethylene glycol; 100 mM NaCl; 10 mM Tris-Cl pH 7.5
  A2: tetraglycol
  First wash buffer: WB11: 50.0% by volume tetraglycol; 2.5 M GuHCl
  Second wash buffer: WB6: 72.0% by volume tetraglycol; 100 mM NaCl; 10 mM Tris-Cl pH 7.5
  Second wash buffer: WB7: 52.0% by volume tetraglycol; 100 mM NaCl; 10 mM Tris-Cl pH 7.5

FIG. 5A:
Behavior of 1,3-butanediol (A1), used in the BioSprint® 96 DNA Blood Protocol
Left: normalized yields, determined by β-actin qPCR; right: agarose gel with the various samples
  First wash buffer: WB10: 49% by volume 1,3-butanediol; 2.5 M GuHCl
  Second wash buffer: WB2: 74% by volume 1,3-butanediol
  Second wash buffer: WB5: 80% by volume 1,3-butanediol; 100 mM NaCl; 10 mM Tris-Cl pH 7.5
  Second wash buffer: WB7: 51% by volume 1,3-butanediol; 100 mM NaCl; 10 mM Tris-Cl pH 7.5

FIG. 5B:
Behavior of diethylene glycol monoethyl ether, used in the BioSprint® 96 DNA Blood Protocol
Left: normalized yields, determined by β-actin qPCR; right: agarose gel with the various samples
  First wash buffer: QIAGEN Buffer AW1
  First wash buffer: WB 11: 42% by volume diethylene glycol monoethyl ether; 2.5 M GuHCl
  Second wash buffer: WB 1. 98% by volume diethylene glycol monoethyl ether
  Second wash buffer: WB6: 71% by volume diethylene glycol monoethyl ether; 100 mM NaCl; 10 mM Tris-Cl pH 7.5

Figure 6:
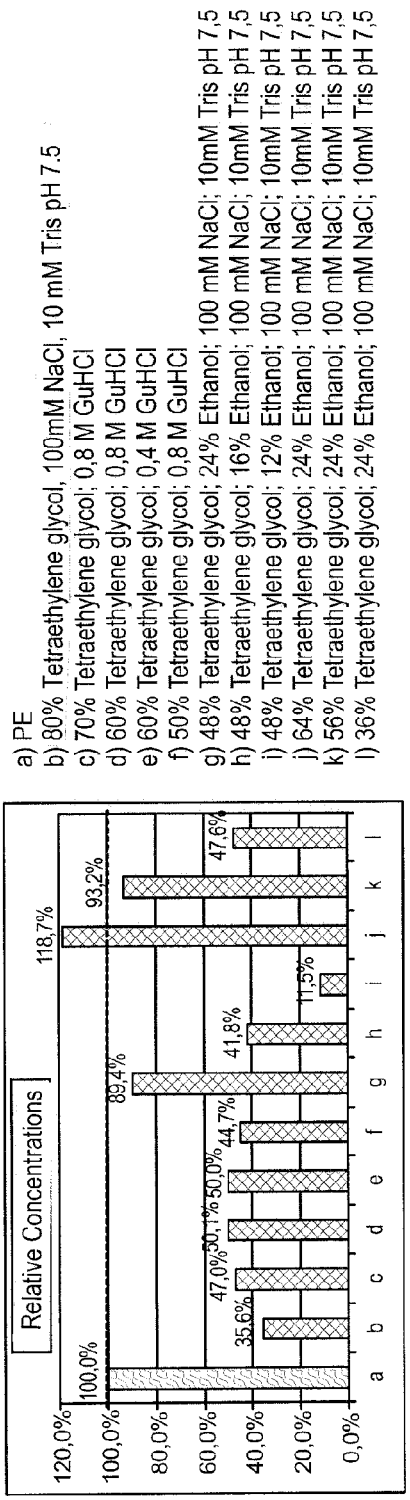

FIG. 6:
QIAquick® purification of the gel pilot 1 kb ladder. The normalized yields are shown. The best wash buffers, as substitute for the commercially available buffer PE, contain 48-64% by volume tetraethylene glycol; 24% by volume ethanol; 100 mM NaCl; 10 mM Tris pH 7.5

Figure 7:
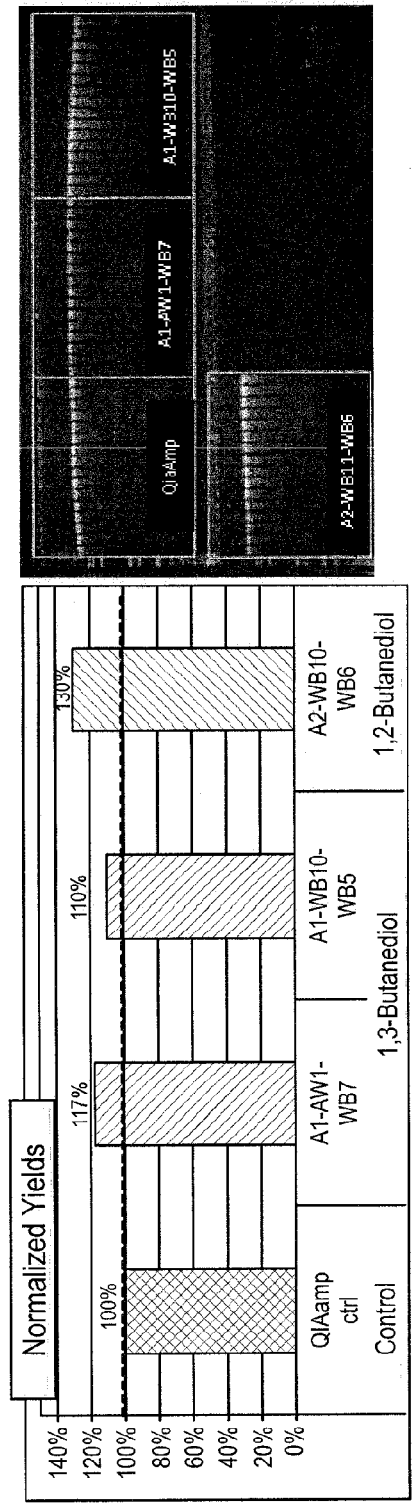
Figure 8:
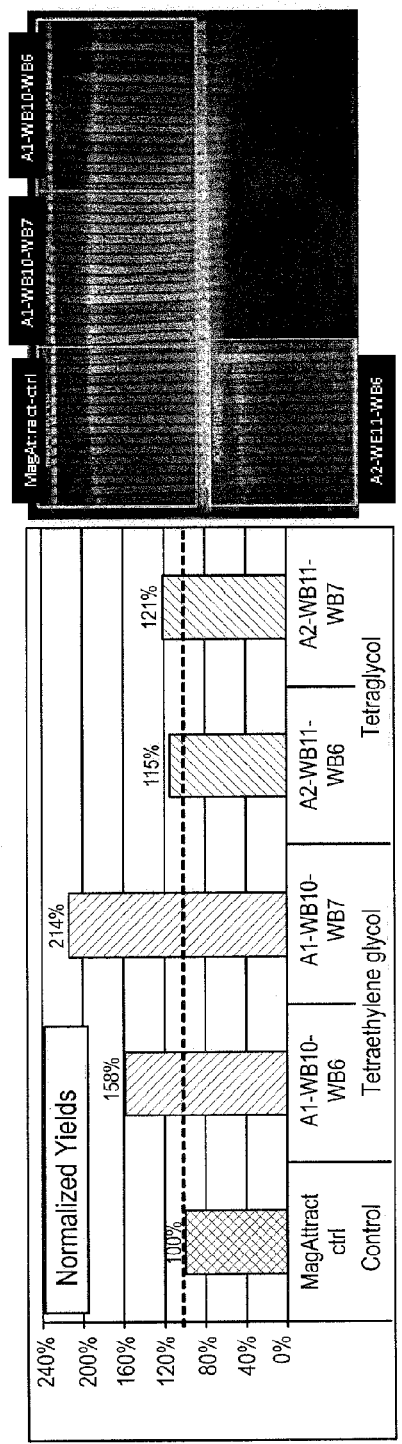
Figure 9:
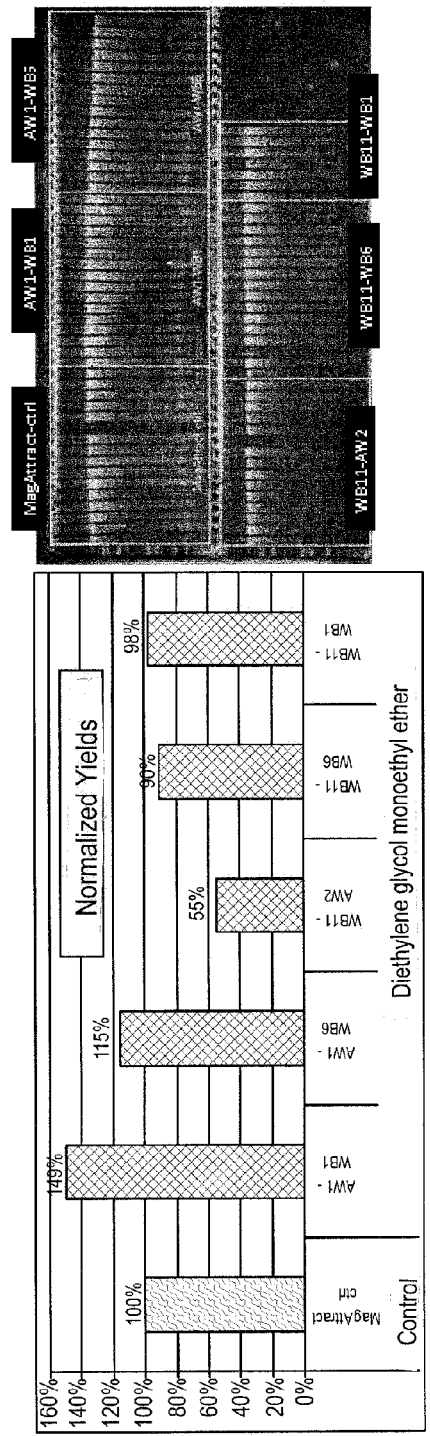
Figure 10:
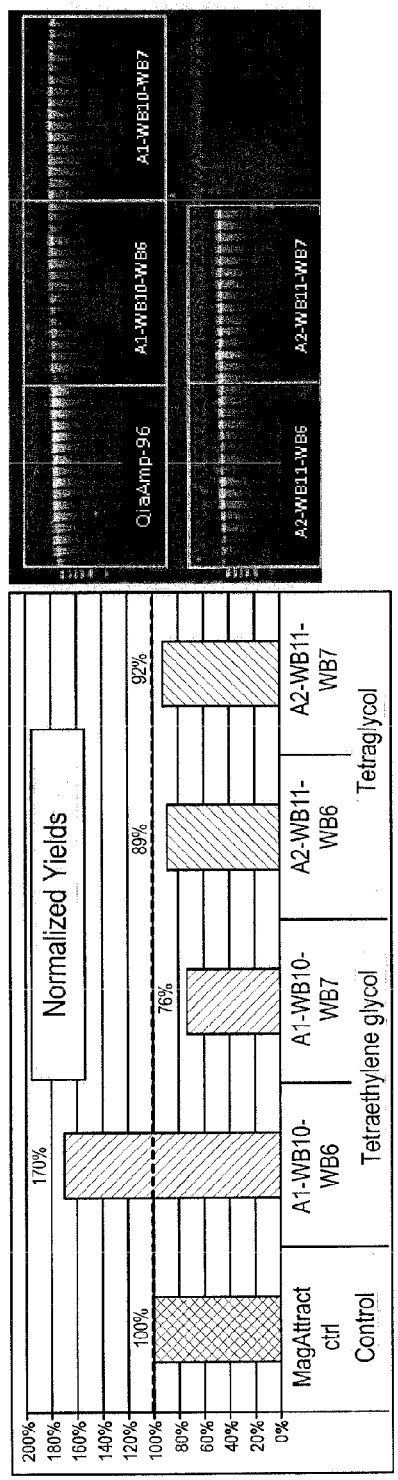
Figure 11:
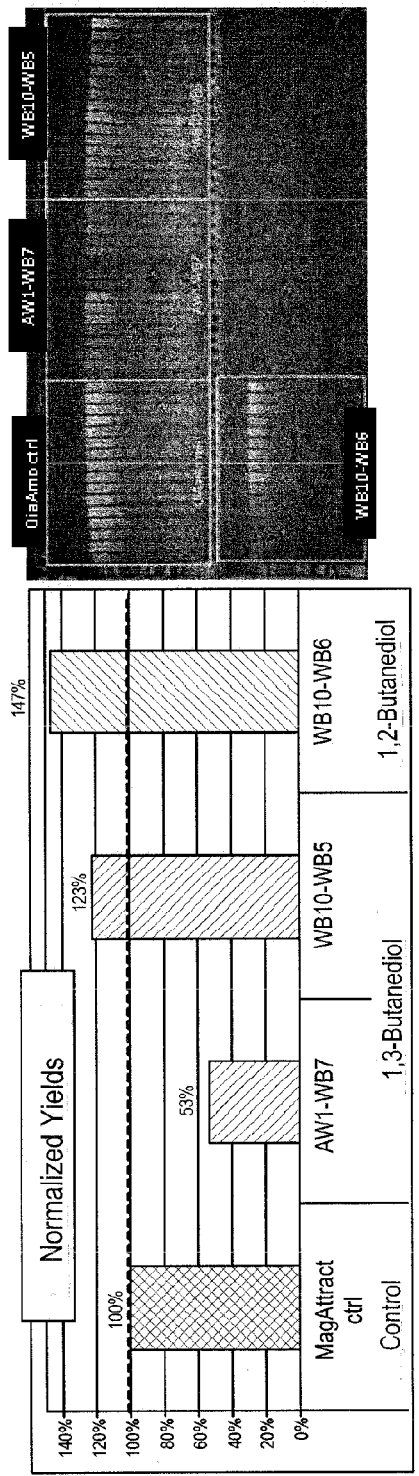
Figure 12:
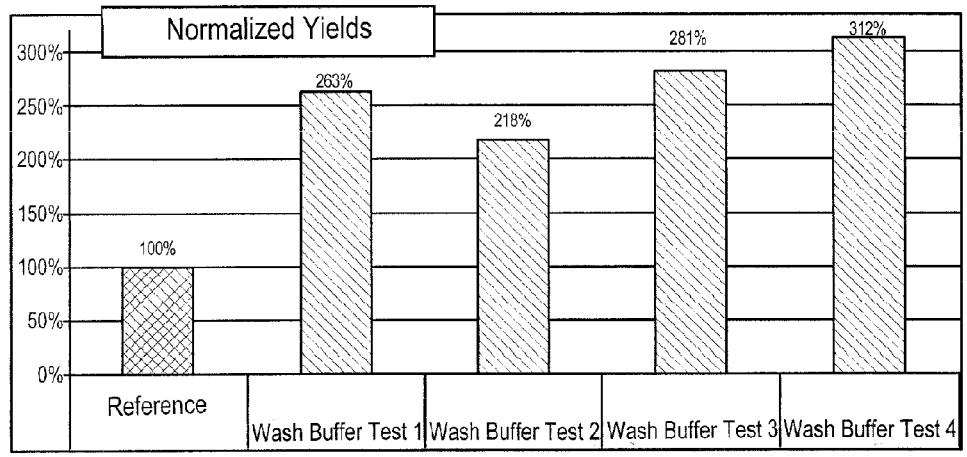
Figure 13:
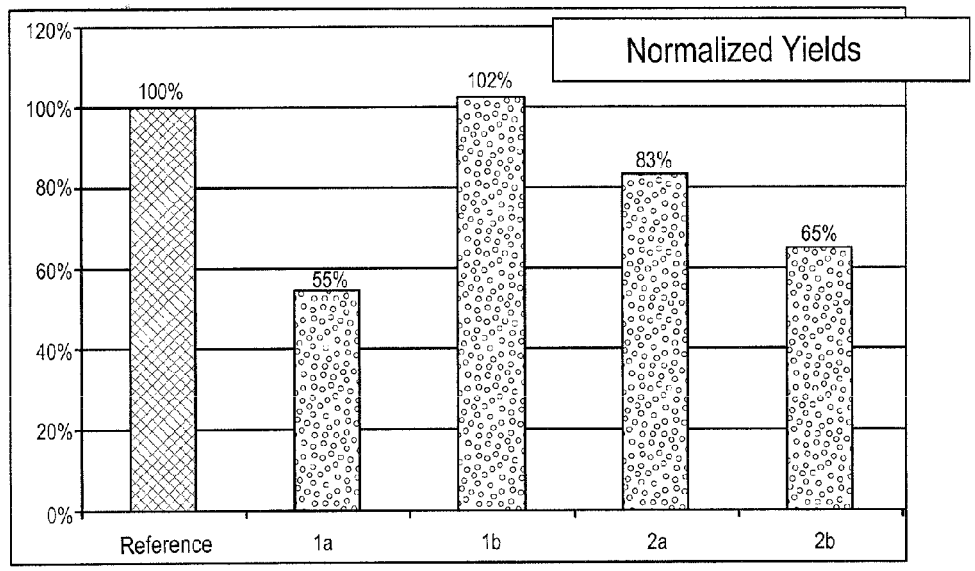
Figure 14:
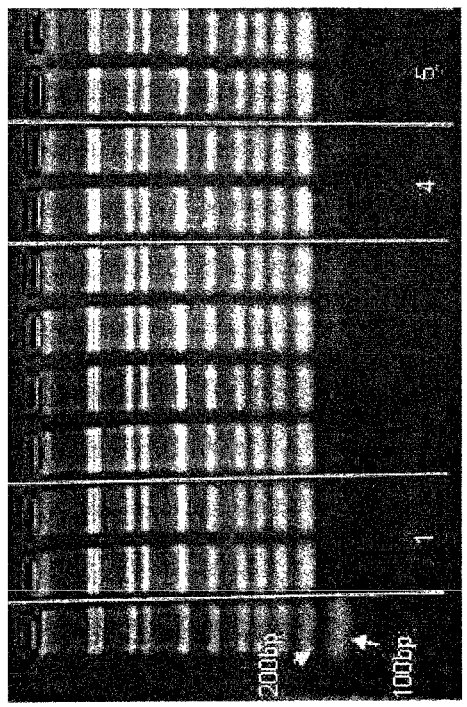
Figure 15:
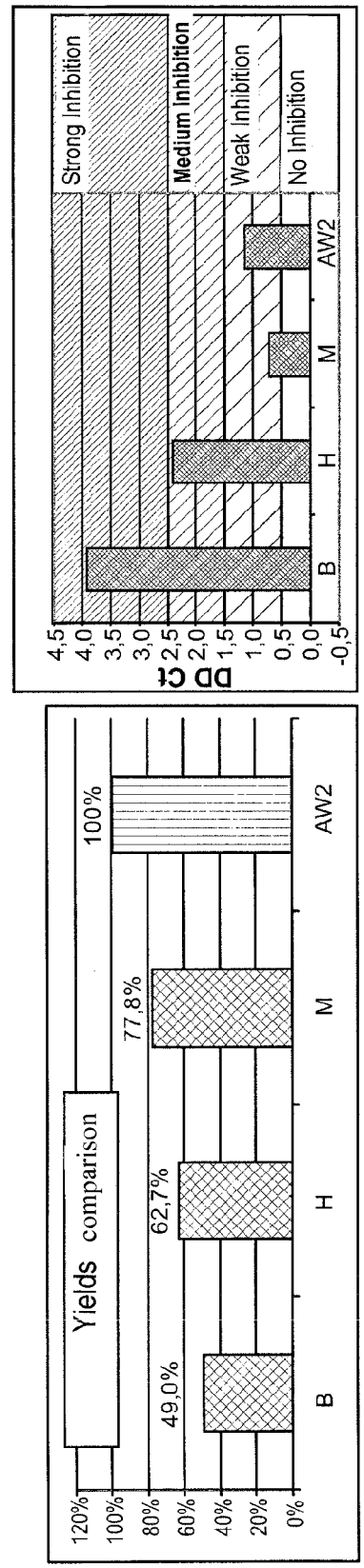
Figure 16:
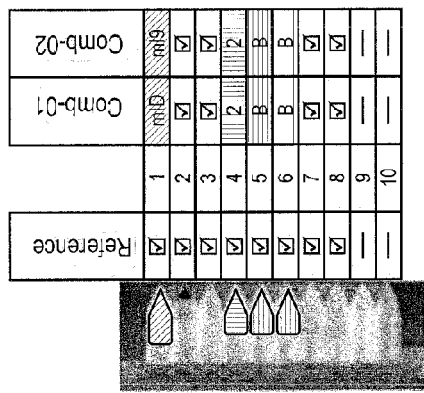
Figure 17:
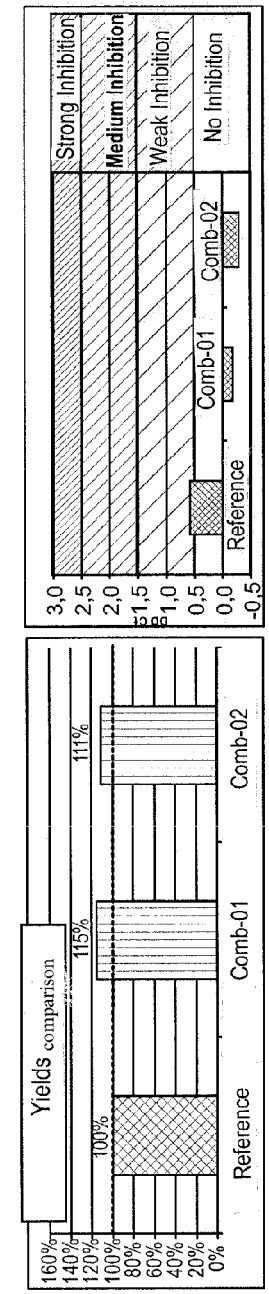
Figure 18:
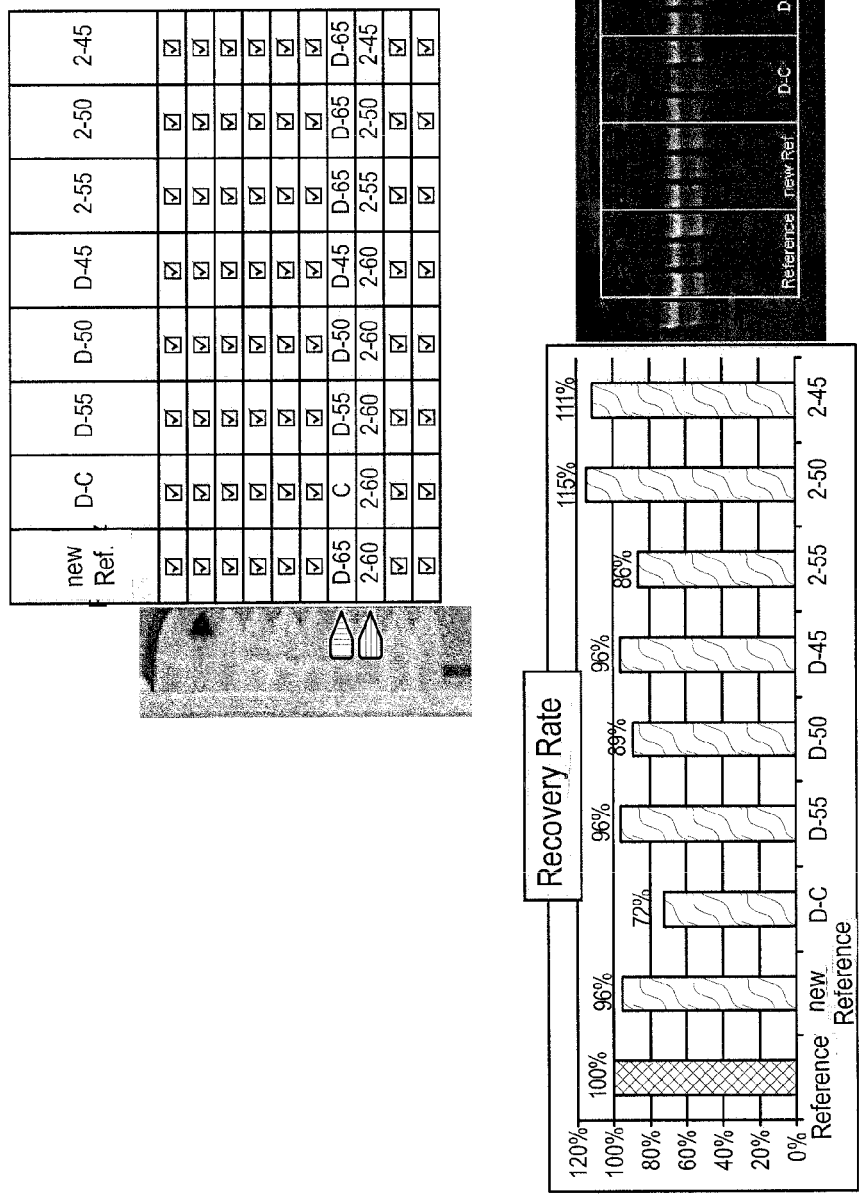
Figure 19:
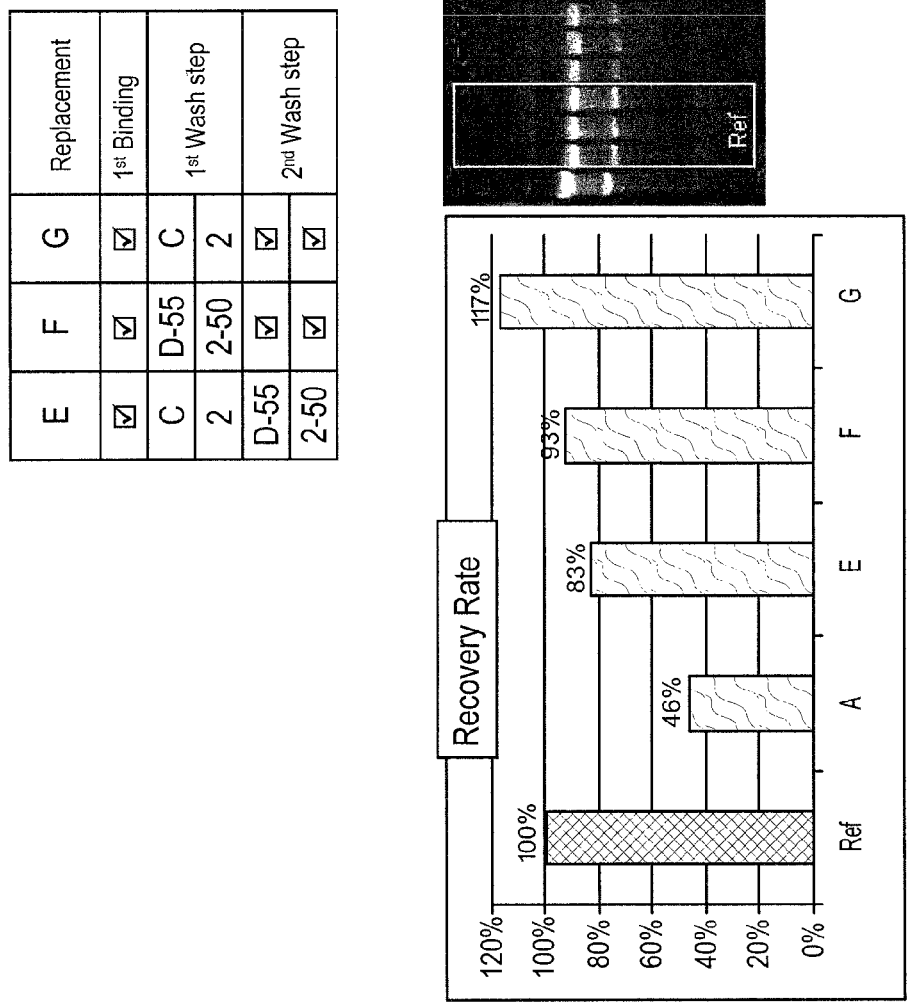
Figure 20:
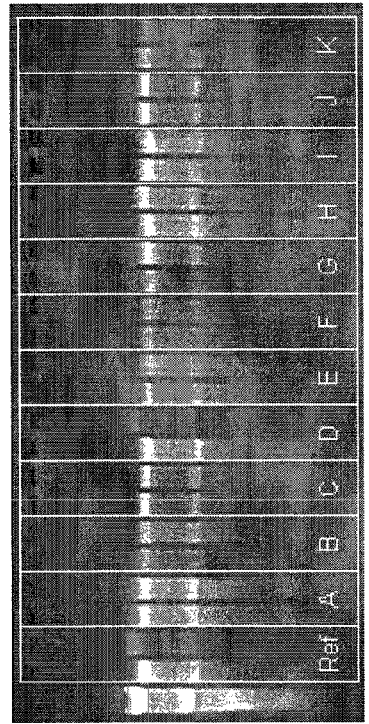
Figure 20:
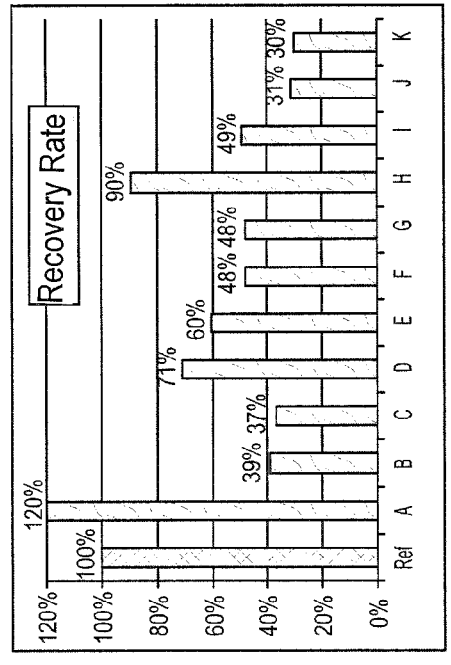
Figure 21:
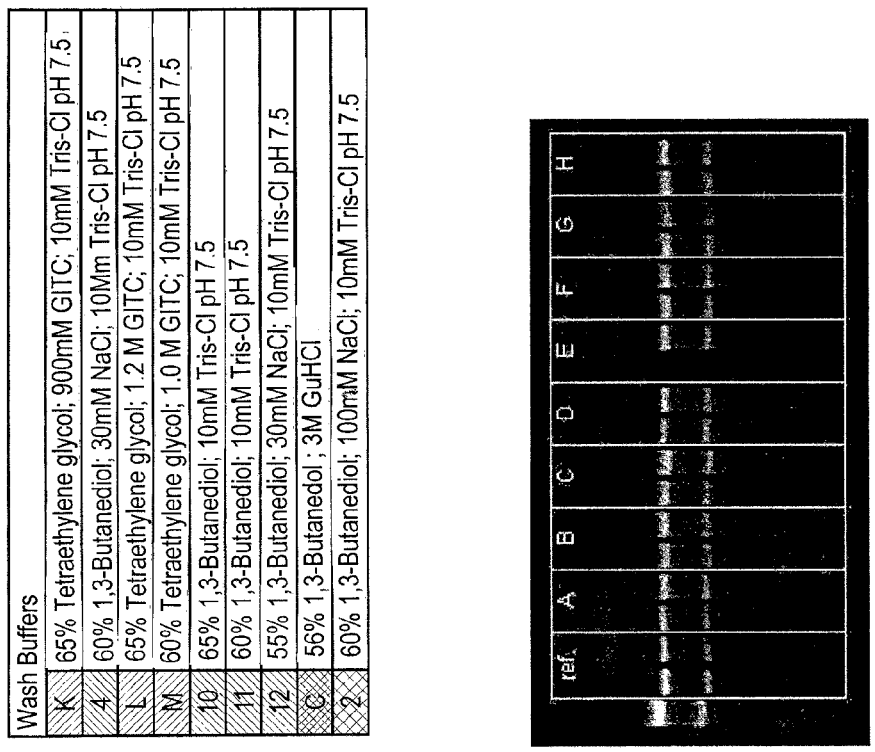
Figure 21:
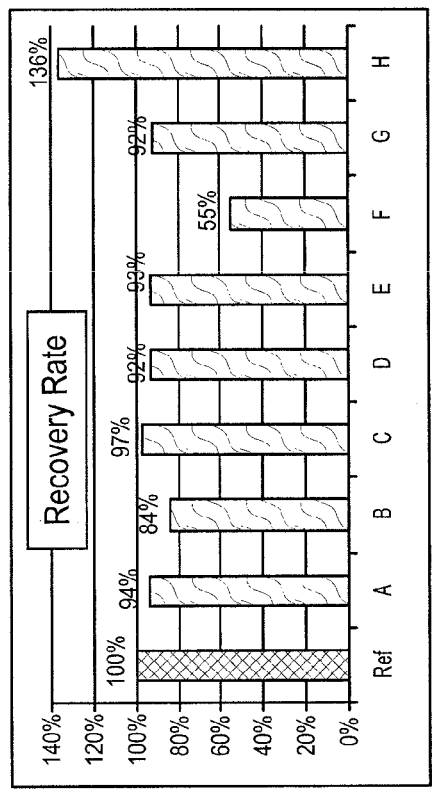

FIG. 7:
Behavior of 1,3-butanediol and 1,2-butanediol, used in the BioSprint® 96 Tissue Protocol Left: normalized yields, determined by Mouse-GapDH qPCR; right: agarose gel
  A1: 1,3-butanediol
  First wash buffer: WB10: 49.0% by volume 1,3-butanediol; 2.5 M GuHCl
  Second wash buffer: WB5: 80.0% by volume 1,3-butanediol; 100 mM NaCl; 10 mM Tris-Cl pH 7.5
  Second wash buffer: WB7: 51.0% by volume 1,3-butanediol; 100 mM NaCl; 10 mM Tris-Cl pH 7.5
  A2: 1,2-butanediol
  First wash buffer: WB10: 49.0% by volume 1,2-butanediol; 2.5 M GuHCl Second wash buffer: WB6: 71.0% by volume 1,2-butanediol; 100 mM NaCl; 10 mM Tris-Cl pH 7.5

FIG. 8:

Behavior of tetraethylene glycol and tetraglycol, used in the BioSprint® 96 Tissue Protocol Left: normalized yields, determined by Mouse-GapDH qPCR; right: agarose gel A1: tetraethylene glycol First wash buffer: WB10: 48.5% by volume tetraethylene glycol; 2.5 M GuHCl Second wash buffer: WB6: 69.8% by volume tetraethylene glycol; 100 mM NaCl; 10 mM Tris-Cl pH 7.5

Second wash buffer: WB7: 50.4% by volume tetraethylene glycol; 100 mM NaCl; 10 mM Tris-Cl pH 7.5

A2: tetraglycol

First wash buffer: WB 11: 50.0% by volume tetraglycol; 2.5 M GuHCl

Second wash buffer: WB6: 72.0% by volume tetraglycol; 100 mM NaCl; 10 mM Tris-Cl pH 7.5

Second wash buffer: WB7: 52.0% by volume tetraglycol; 100 mM NaCl; 10 mM Tris-Cl pH 7.5

FIG. 9:

Behavior of diethylene glycol monoethyl ether, used in the BioSprint® 96 Tissue Protocol Left: normalized yields, determined by Mouse-GapDH qPCR; right: agarose gel First wash buffer: WB11: 42% by volume diethylene glycol monoethyl ether; 2.5 M GuHCl First wash buffer: buffer AW1

Second wash buffer: WB1: 98% by volume diethylene glycol monoethyl ether

Second wash buffer: WB6: 71% by volume diethylene glycol monoethyl ether; 100 mM NaCl; 10 mM Tris-Cl pH 7.5

FIG. 10:

Behavior of tetraethylene glycol and tetraglycol, used in the DNeasy® 96 Tissue Protocol Left: normalized yields, determined by Mouse-GapDH qPCR; right: agarose gel A1: tetraethylene glycol First wash buffer: WB10: 48.5% by volume tetraethylene glycol; 2.5 M GuHCl Second wash buffer: WB6: 69.8% by volume tetraethylene glycol; 100 mM NaCl; 10 mM Tris-Cl pH 7.5

Second wash buffer: WB7: 50.4% by volume tetraethylene glycol; 100 mM NaCl; 10 mM Tris-Cl pH 7.5

A2: tetraglycol

First wash buffer: WB 11: 50.0% by volume tetraglycol; 2.5 M GuHCl

Second wash buffer: WB6: 72.0% by volume tetraglycol; 100 mM NaCl; 10 mM Tris-Cl pH 7.5

Second wash buffer: WB7: 52.0% by volume tetraglycol; 100 mM NaCl; 10 mM Tris-Cl pH 7.5

FIG. 11:

Behavior of 1,3-butanediol and 1,2-butanediol, used in the BioSprint® 96 Tissue Protocol Left: normalized yields, determined by Mouse-GapDH qPCR; right: agarose gel A1: 1,3-butanediol First wash buffer: WB10: 49.0% by volume 1,3-butanediol; 2.5 M GuHCl Second wash buffer: WB5: 80.0% by volume 1,3-butanediol; 100 mM NaCl; 10 mM Tris-Cl pH 7.5

Second wash buffer: WB7: 51.0% by volume 1,3-butanediol; 100 mM NaCl; 10 mM Tris-Cl pH 7.5

A2: 1,2-butanediol

First wash buffer: WB10: 49.0% by volume 1,2-butanediol; 2.5 M GuHCl

Second wash buffer: WB6: 71.0% by volume 1,2-butanediol; 100 mM NaCl; 10 mM Tris-Cl pH 7.5

FIG. 12:

Behavior of tetraethylene glycol and 1,3-butanediol, used in the RNeasy®96 Protocol Normalized yields, determined by Lamin RT-qPCR; with "293" cells being used

FIG. 13:

Behavior of various ethanol-replacing chemicals, used in the RNeasy® 96 Protocol Left: normalized yields, determined by Mouse-GapDH qPCR; right: agarose gel Binding additive "1" 98% by volume TetraGlyme "2" 73.5% by volume TetraGlyme; 24% by volume ethanol Washing combination "a":

First wash buffer: 20% by volume tetraethylene glycol; 900 mM GTC; 10 mM Tris/Cl pH 7.5;

Second wash buffer: 70% by volume tetraethylene glycol; 100 mM NaCl; 10 mM Tris-Cl pH 7.5

Washing combination "b":

First wash buffer: 20% by volume 1,3-butanediol; 900 mM GTC; 10 mM Tris/Cl pH 7.5

Second wash buffer: 80% by volume 1,3-butanediol; 100 mM NaCl; 10 mM Tris-Cl pH 7.5

FIG. 14:

Fragment Size Exclusion Experiment

RNeasy® excludes small RNAs (5,8 S; tRNA; miRNA; . . . ) during purification. The threshold is at about 150 bases. This experiment shows that the size exclusion of the tested chemicals is comparable to ethanol as reference.

Wa: 20% by volume 1,3-butanediol; 900 mM GTC; 10 mM Tris/Cl pH 7.5

Wb: 60% by volume 1,3-butanediol; 100 mM NaCl; 10 mM Tris-Cl pH 7.5

FIG. 15:

Behavior of various ethanol-replacing chemicals, used in the EpiTect Purification Protocol Left: normalized yields, determined by CFF1 qPCR; right: "Delta Delta Ct" analysis of different sample volumes. The calculation compares the measured Delta Ct values with the theoretical Delta Ct values, which leads to a numerical value of the degree of PCR inhibition.

B 90% by volume tetraethylene glycol; 10 mM Tris-Cl pH 7.5

H 72% by volume 1,3-butanediol; 100 mM NaCl; 10 mM Tris-Cl pH 7.5

M 60% by volume diethylene glycol monoethyl ether; 100 mM NaCl; 10 mM Tris-Cl pH 7.5

FIG. 16:

Cartridge Assembly

Buffer ML mlD 4.5 M GTC; 50 mM $NH_4Cl$; 45 mM Tris pH 7.5; 20 mM EDTA; 2.0% by volume Triton-X-100 ml9 4.5 M GTC; 1.0 M NaCl; 50 mM $NH_4Cl$; 45 mM Tris pH 7.5; 20 mM EDTA; 2.0% by volume Triton-X-100

MW1 Replacement buffer of the present invention 2 49% by volume 1,3-butanediol; 2.5 MGuHCl MW2 Replacement buffer of the present invention B 60% by volume 1,3-butanediol; 100 mM NaCl; 10 mM Tris-Cl pH 7.5

FIG. 17:

Behavior of various ethanol-replacing chemicals, used in the EZ1® DNA Blood 200 μl Protocol Top left: normalized yields, determined by β-actin qPCR; right: "Delta Delta Ct" analysis of different sample volumes. The calculation compares the measured Delta Ct values with the theoretical Delta Ct values, which leads to a numerical value for the degree of PCR inhibition. Bottom left: agarose gel

FIG. 18:

Behavior of various ethanol-replacing chemicals, used in the second wash step (subsequent to DNAse digestion) of the EZ1®—RNA Protocol Left: cartridge assembly; bottom left: normalized yields, determined by MapK2 RT qPCR; bottom right: agarose gel MW1 replacement buffers of the present invention "C" 56% by volume 1,3-butanediol; 3 M GuHCl "D-65" 65% by volume 1,3-butanediol; 1.75 M GuHCl "D-55" 55% by volume 1,3-butanediol; 1.75 M GuHCl "D-50" 50% by volume 1,3-butanediol; 1.75 M GuHCl "D-45" 45% by volume 1,3-butanediol; 1.75 M GuHCl Buffer RPE replacement buffers of the present invention "2-60" 60% by volume 1,3-butanediol; 100 mM NaCl; 10 mM Tris-Cl pH 7.5

"2-55" 55% by volume 1,3-butanediol; 100 mM NaCl; 10 mM Tris-Cl pH 7.5

"2-50" 50% by volume 1,3-butanediol; 100 mM NaCl; 10 mM Tris-Cl pH 7.5

"2-45" 45% by volume 1,3-butanediol; 100 mM NaCl; 10 mM Tris-Cl pH 7.5

FIG. 19:

Behavior of various ethanol-replacing chemicals, used in the first and the second wash steps of the EZ1®—RNA Protocols Top: cartridge assembly; left: normalized yields, determined by MapK2 RT qPCR; bottom: agarose gel MW1 replacement buffer of the present invention "C" 56% by volume 1,3-butanediol; 3 M GuHCl "D-55" 55% by volume 1,3-butanediol; 1.75 M GuHCl Buffer RPE replacement buffer of the present invention "2" 60% by volume 1,3-butanediol; 100 mM NaCl; 10 mM Tris-Cl pH 7.5

"2-50" 50% by volume 1,3-butanediol; 100 mM NaCl; 10 mM Tris-Cl pH 7.5

FIG. 20:

Behavior of various ethanol-replacing chemicals, used in the first and second wash steps of the EZ1®—RNA Protocol.

Top: cartridge assembly; left: normalized yields, determined by MapK2 RT qPCR; bottom right: agarose gel

FIG. 21:

Behavior of various ethanol-replacing chemicals, used in the first and second wash steps of the EZ1®—RNA Protocol.

Top: cartridge assembly; left: normalized yields, determined by MapK2 RT qPCR; bottom right: agarose gel

FIG. 22A:

Exemplary EZ1 Cartridge Layout according to Table 1.

FIG. 22B:

Exemplary EZ1 Cartridge Layout according to Table 3.

The following examples are intended to describe the invention in more detail:

1. Chemicals and Test Kits/Test Protocols with Wash Buffers of the Invention 1.1 Chemicals (Table):

| Name | CAS |
|---|---|
| Tetraglycol, liquid, pure | 9004-76-6 |
| Tetraethylene glycol, purum, 97% by volume | 112-60-7 |
| 1,3-Butanediol, purum, 98% by volume | 107-88-0 |
| 1,2-Butanediol, purum, 98% by volume | 584-03-2 |
| Diethylene glycol monoethyl ether, 99% by volume | 111-90-0 |

1.2 Test Kits/Test Protocols 1.2.1 "BioSprint® 96 DNA Blood"

BioSprint® 96 with Protocol File: "BS96_DNA_Blut_200"

Lysis

200 μl blood

200 μl buffer AL

20 μl QIAGEN Protease incubation for 15 min at 56° C. and 1400 rpm on a thermomixer Binding add 200 μl isopropanol add 30 μl MagAttract® Suspension G (QIAGEN GmbH)

Wash Solutions

Reference Protocol

1× buffer AW1 (650 μl)

1× buffer AW1 (500 μl)

2× buffer AW2 (500 μl)

Buffer AW 1 replacement buffers of the present invention

50% by volume tetraglycol; 2.5 M GuHCl 48.5% by volume tetraethylene glycol; 2.5 M GuHCl 49% by volume 1,3-butanediol; 2.5 M GuHCl 49% by volume 1,2-butanediol; 2.5 M GuHCl 42% by volume diethylene glycol monoethyl ether; 2.5 M GuHCl Buffer AW2 replacement buffers of the present invention 52% by volume tetraglycol; 100 mM NaCl; 10 mM Tris-Cl pH 7.5

69.8% by volume tetraethylene glycol; 100 mM NaCl; 10 mM Tris-Cl pH 7.5

80% by volume 1,3-butanediol; 100 mM NaCl; 10 mM Tris-Cl pH 7.5

71% by volume 1,2-butanediol; 100 mM NaCl; 10 mM Tris-Cl pH 7.5

71% by volume diethyleneglycol monoethyl ether; 100 mM NaCl; 10 mM Tris-Cl pH 7.5

Aqueous solution: 0.02% by volume Tween 20

Elution: 200 μl μl RNase-free water in MicroTubePacl-MicroPlate 1.2.2 QIAamp® 96 Spin Blood Protocol Lysis 200 μl blood 200 μl buffer AL 20 μl QIAGEN Protease Incubation 15 min at 56° C.

Binding

Add 200 μl ethanol

Mix in S block and transfer to QIAamp® 96 plate

Wash Solutions

Reference Methods

1× buffer AW1 (650 μl)

1× buffer AW2 (500 μl)

Buffer AW1 replacement solutions of the present invention
    49% by volume 1,3-butanediol; 2.5 M GuHCl
    49% by volume 1,2-butanediol; 2.5 M GuHCl
    42% by volume diethylene glycol monoethyl ether; 2.5 M GuHCl
    50% by volume tetraglycol; 2.5 M GuHCl
    48.5% by volume tetraethylene glycol; 2.5 M GuHCl
Buffer AW2 replacement solutions of the present invention
    80% by volume 1,3-butanediol; 100 mM NaCl; 10 mM Tris-Cl pH 7.5
    71% by volume 1,2-butanediol; 100 mM NaCl; 10 mM Tris-Cl pH 7.5
    71% by volume diethylene glycol monoethyl ether; 100 mM NaCl; 10 mM Tris-Cl pH 7.6
    52% by volume tetraglycol; 100 mM NaCl; 10 mM Tris-Cl pH 7.5
    50.4% by volume tetraethylene glycol; 100 mM NaCl; 10 mM Tris-Cl pH 7.5
Elution: 200 μl μl RNase-free water in elution microtube rack 1.2.3 "BioSprint® 96 DNA Tissue"
BioSprint®-96 Protocol file: "BS96_DNA_Blut_200"
Lysis
200 μl lysate (25 mg Tissue+180 μl buffer ATL+20 μl proteinase K, over night incubation 56° C.)
+200 μl buffer AE
Binding
Add 200 μl isopropanol
+30 μl MagAttract® Suspension G
Wash Solutions
1× buffer AW1 (650 μl)
1× buffer AW1 (500 μl)
2× buffer AW2 (500 μl)
Buffer AW1 replacement solutions of the present invention
    48.5% by volume tetraethylene glycol; 2.5 M GuHCl
    50% by volume 1,2-butanediol; 2.5 M GuHCl
    50% by volume tetraglycol; 2.5 M GuHCl
    49% by volume 1,3-butanediol; 2.5 M GuHCl
    42% by volume diethylene glycol monoethyl ether; 2.5 M GuHCl
Buffer AW2 replacement solutions of the present invention
    50.4% by volume tetraethylene glycol; 100 mM NaCl; 10 mM Tris-Cl pH 7.5
    52% by volume 1,2-butanediol; 100 mM NaCl; 10 mM Tris-Cl pH 7.5
    52% by volume tetraglycol; 100 mM NaCl; 10 mM Tris-Cl pH 7.5
    80% by volume 1,3-butanediol; 100 mM NaCl; 10 mM Tris-Cl pH 7.5
    98% by volume diethylene glycol monoethyl ether, pure solution
Aqueous solution: 0.02% by volume Tween® 20 (500 μl)
Elution: 200 μl RNase-free water in microtube plate 1.2.4 "DNeasy® 96 Tissue"
Lysis
200 μl lysate (25 mg tissue+180 μl buffer ATL+20 μl proteinase K, overnight incubation 56° C.)
+200 μl buffer AE
Binding
add 200 μl ethanol
mix in the S block and transfer to QIAamp® 96-Plate
Wash Solutions
1× buffer AW1 (650 μl)
1× buffer AW2 (500 μl)
Buffer AW1 replacement solutions of the present invention
    48.5% by volume tetraethylene glycol; 2.5 M GuHCl
    49% by volume 1,2-butanediol; 2.5 M GuHCl
    49% by volume 1,3-butanediol; 2.5 M GuHCl
    50% by volume tetraglycol; 2.5 M GuHCl
Buffer AW2 replacement solutions of the present invention
    69.8% by volume tetraethylene glycol; 100 mM NaCl; 10 mM Tris-Cl pH 7.5
    71% by volume 1,2-butanediol; 100 mM NaCl; 10 mM Tris-Cl pH 7.5
    80% by volume 1,3-butanediol; 100 mM NaCl; 10 mM Tris-Cl pH 7.5
    52% by volume tetraglycol; 100 mM NaCl; 10 mM Tris-Cl pH 7.5
Elution: 200 μl RNase-free water in elution micro tubes 1.2.5 RNeasy® 96
Binding
350 μl buffer RLT—lysate ("293" cells; 2×10$^5$ cells/sample)
add 350 μl ethanol
mix in the S block and transfer to RNeasy® 96-Plate
Wash Solutions
2× buffer RW1 (650 μl)
2× buffer RPE (500 μl)
Buffer RW1 replacement solutions of the present invention
    20% by volume 1,3-butanediol; 900 mM GTC; 10 mM Tris-Cl pH 7.5
    20% by volume tetraethylene glycol; 900 mM GTC; 10 mM Tris-Cl pH 7.5
Buffer RPE replacement solutions of the present invention
    80% by volume 1,3-butanediol; 100 mM NaCl; 10 mM Tris-Cl pH 7.5
    60% by volume tetraethylene glycol; 100 mM NaCl; 10 mM Tris-Cl pH 7.5
Elution: 100 μl RNase-free water in elution micro tubes 1.2.6 QIAquick®
Binding
1 volume of sample
add 5 volumes of buffer PM (Standard Reference Protocol)
load onto QIAamp® MinElute column; 1'@8000 rpm
Wash Solution
1× wash solution: A; 1'@8000 rpm
    Buffer PM replacement solution of the present invention
        64% by volume tetraethylene glycol; 24% by volume ethanol; 100 mM NaCl; 10 mM Tris pH 7.5
dry centrifugation
elution 40 μl RNase-free water; 1'@8000 rpm 1.2.7 No Hazardous Material—Modified EpiTect Bisulfite Protocol
1) Bisulfite DNA conversion according to the handbook EpiTect Bisulfite Kit of the company QIAGEN GmbH
2) Purification of bisulfite converted DNA Step #:
    6. Transfer the complete bisulfite reactions to clean 1.5 ml microcentrifuge tubes. Any precipitants in the solution will not affect the performance or yield of the reaction.
    7. Add 560 μl freshly prepared Buffer BL containing 10 μg/ml carrier RNA. Mix the solution by vortexing.
    Note: Carrier DNA is not necessary when using >100 ng DNA.
    8. Transfer the whole mixture into the EpiTect® spin column.
    9. Centrifuge the column at maximum speed for 1 min. Discard the flow-through, and place the spin column back into the collection tube.

10. Add 500 µl Buffer BW (wash buffer) to the spin column, and centrifuge at maximum speed for 1 min. Discard the flow-through, and place the spin column back into the collection tube.

11. Add 500 µl Buffer BD (desulfonation buffer) to the spin column, and incubate for 15 min at room temperature. If there are precipitates in Buffer BD, avoid transferring them to the spin column. Note: It is important to close the lid of the column before incubation.

12. Centrifuge the column at maximum speed for 1 min. Discard the flow-through, and place the spin column back into the collection tube.

13. Add 500 µl Buffer BW and centrifuge at maximum speed for 1 min. Discard the flow-through, and place the spin column back into the collection tube.

14. Repeat step 13 once.

15. Place the spin column into a new 2 ml collection tube, and centrifuge the spin column at maximum speed for 1 min to remove any residual liquid. Note: If the purified DNA is intended for use in real-time PCR, extend the centrifugation time to 5 min.

16. Place the spin column into a clean 1.5 ml microcentrifuge tube. Add 20 µl Buffer EB to the center of the membrane. Elute the purified DNA by centrifugation for 1 min at approximately 15,000×g (12,000 rpm).

Buffer BW replacement solutions of the present invention for Step 13 of the protocol 60% by volume diethylene glycol monoethyl ether; 100 mM NaCl; 10 mM Tris-Cl pH 7.5

72% by volume 1,3-butanediol; 100 mM NaCl; 10 mM Tris-Cl pH 7.5

1.2.8 EZ1® DNA Blood 200 µl Protocol
EZ1 Cartridge Layout

TABLE 1

| Recess No. | EZ1 Blood 200 µl Kit Reagent Cartridge, Blood 200 µl Kit Components for a Cartridge | Volume (µl) | Exchange Position |
|---|---|---|---|
| 1 | Lysis Buffer (Buffer ML) | 740 | ← |
| 2 | Diluted Bead Suspension | 300 | |
| 3 | Bead Buffer | 60 | |
| 4 | Washing Solution I (Buffer MW1-EtOH) | 900 | ← |
| 5 | Washing Solution II (Buffer MW2-EtOH) | 900 | ← |
| 6 | Washing Solution II (Buffer MW2-EtOH) | 900 | ← |
| 7 | Rinse (RNAse-free Water) | 1000 | |
| 8 | Elution Buffer (RNAse-free Water) | 220 | |
| 9 | Vacant | 0 | |
| 10 | Vacant | 1000 | |

EZ1 DNA blood Card Version 1.30
FIG. 22A demonstrates an exemplary cartridge laid out according to Table 1.

TABLE 2

Replacement Buffer

| ML Replacement Buffer | Position |
|---|---|
| 4.5 M GTC; 1.0 M NaCl; 50 mM NH₄Cl; 45 mM Tris pH 7.5; 20 mM EDTA; 2.0% Triton-X-100 | 1 |
| 4.5 M GTC; 50 mM NH₄Cl; 45 mM Tris pH 7.5; 20 mM EDTA; 2.0% Triton-X-100 | 1 |
| MW1 Replacement Buffer | Position |
| 49% 1,3-Butanediol; 2.5 M GuHCl | 4 |
| MW2 Replacement Buffer | Position |
| 60% 1,3-Butanediol; 100 mM NaCl; 10 mM Tris-Cl pH 7.5 | 4 + 6 |

1.2.9 EZ1®—RNA Protocol
EZ1 Cartridge Layout

TABLE 3

| Recess No. | EZ1 RNA Cell New Version Reagent Cartridge, RNA from Cells | Volume (µl) | Exchange Position |
|---|---|---|---|
| 1 | RPE + 96% EtOH (=RPE Working Solution) | 400 + 100 | ← |
| 2 | 0.5 M LiCl + MagAttr. Susp. B | 320 + 80 | |
| 3 | MW + 96% EtOH (=AW1 Working Solution) | 344 + 456 | ← |
| 4 | RPE + 96% EtOH (=RPE Working Solution) | 160 + 640 | ← |
| 5 | RDD | 245 | |
| 6 | MW (=AW1 Concentrate) | 250 | |
| 7 | MW + 96% EtOH (=AW1 Working Solution 2) | 251 + 785 | ← |
| 8 | RPE + 96% EtOH | 180 + 720 | ← |
| 9 | RNAse-free H2O | 1000 | |
| 10 | RNAse-free H2O | 200 | |

EZ1 RNA Card Version 2.081
FIG. 22B demonstrates an exemplary cartridge laid out according to Table 3.

TABLE 4

Replacement Buffers

| Binding Additives | Position |
|---|---|
| Tetraethylene glycol (99%) | 1 |
| 1,3-Butanediol (98%) | 1 |
| 80% Diethylene glycol monoethyl acetate; 16% Ethanol | 1 |

| Wash Buffer | Position |
|---|---|
| 56% 1,3-Butanediol; 3 M GuHCl | 3 |
| 60% 1,3-Butanediol; 100 mM NaCl; 10 mM Tris-Cl pH 7.5 | 4 |
| 65% Tetraethylene glycol ; 900 mM GTC; 10 mM Tris/HCL pH 7.5 | 7 |
| 60% 1,3-Butanediol ; 30 mM NaCl; 10 mM Tris-Cl pH 7.5 | 8 |

2. Results

The results obtained with the test kits/test protocols of the invention are shown in FIGS. 1 to 21.

The studies shown herein focus on the ethanol-replacing chemicals in wash buffers for the silica-mediated preparation of nucleic acids. The tested sample material ranged from blood to tissues as well as purification products from a nucleic acid modification reaction. In addition, the purification of various types of nucleic acids was tested (genomic DNA; total RNA; small double-stranded DNA fragments). The identified chemicals were tested with methods using columns with silica-based membranes or silica-coated magnetic particles.

Chemical
CAS
Concentration/Buffer Compositions of the Replacement Solutions of the Present Invention
Used in the Examples 1,2-butanediol [1,2-Butanediol]
584-03-2
49% by volume 1,2-butanediol; 2.5 M GuHCl
71% by volume 1,2-butanediol; 100 mM NaCl; 10 mM Tris-Cl pH 7.5

1,2-propanediol
57-55-6
99% by volume 1,2-propanediol
74% by volume 1,2-propanediol, 100 mM NaCl; 10 mM Tris-Cl pH 7.5

1,3-Butanediol 107-88-0
49% by volume 1,3-butanediol; 2.5 M GuHCl
56% by volume 1,2-butanediol; 3 M GuHCl
20% by volume 1,3-butanediol; 900 mM GTC; 10 mM Tris-Cl pH 7.5
72-80% by volume 1,3-butanediol; 30-100 mM NaCl; 10 mM Tris-Cl pH 7.5
1-Methoxy-2-propanol acetate [2-methoxy-1-methylethyl acetate]
108-65-6
100% by volume 1-methoxy-2-propanol acetate
3-Methyl-1,3,5-pentanetriol
7564-64-9
80-40% by volume 3-methyl-1,3,5-pentanetriol
60% by volume 3-methyl-1,3,5-pentanetriol, 100 mM NaCl; 10 mM Tris-Cl pH 7.5
DBE-2 dibasic ester
MFCD00191969
100-50% by volume DBE-2
DBE-3 dibasic ester
MFCD00191969
100-50% by volume DBE-3
DBE-4 dibasic ester [dimethyl succinate]
106-65-0
100-50% by volume DBE-4
DBE-5 dibasic ester [dimethyl glutarate]
1119-40-0
100-50% by volume DBE-5
DBE-6 dimethyl adipate [dibasic ester; dimethyl adipate]
627-93-0
100-50% by volume DBE-5
Diethylene glycol monoethyl ether (DGME) [ethyldiglycol]
111-90-0
42% by volume DGME; 2.5 M GuHCl
71% by volume DGME; 100 mM NaCl; 10 mM Tris-Cl pH 7.5
Diethylene glycol monoethyl ether acetate (DGMEA) [Ethyl diglycol acetate]
112-15-2
99.0% by volume DGMEA
50-80% by volume DGMEA; 100 mM NaCl; 10 mM Tris-Cl pH 7.5
Ethyl lactate
97-64-3
100% by volume ethyl lactate
75% by volume ethyl lactate, 100 mM NaCl; 10 mM Tris-Cl pH 7.5
Ethylene glycol
107-21-1
100% by volume ethylene glycol
Poly(2-ethyl-2-oxazoline) [2-ethyl-4,5-dihydro-1,3-oxazole]
25805-17-8
23% by volume poly(2-ethyl-2-oxazoline), 100 mM NaCl; 10 mM Tris-Cl pH 7.5
Poly(4-styrene sulfonic acid-co-maleic acid) 68037-40-1
25% by volume poly(4-styrene sulfonic acid-co-maleic acid)
19% by volume poly(4-styrene sulfonic acid-co-maleic acid)
100 mM NaCl; 10 mM Tris-Cl pH 7.5
Tetraethylene glycol (TEG)
112-60-7
48.5% by volume TEG; 2.5 M GuHCl
20-65% by volume TEG; 900 mM GTC; 10 mM Tris-Cl pH 7.5
50.4-60% by volume TEG; 100 mM NaCl; 10 mM Tris-Cl pH 7.5
64% by volume TEG, 24% by volume ethanol;
50% by volume TEG, 50% by volume poly(propylene glycol), MW~725 (CAS 25322-69-4)
Tetraglycol
9004-76-6
50% by volume tetraglycol; 2.5 M GuHCl
52% by volume tetraglycol; 100 mM NaCl; 10 mM Tris-Cl pH 7.5
Tetrahydrofurfuryl polyethylene glycol 200
31692-85-0
100% by volume (purum)
75% by volume tetrahydrofurfuryl PEG 200, 100 mM NaCl; 10 mM Tris-Cl pH 7.5
Tri(ethylene glycol) divinyl ether
765-12-8
75-98% by volume tri(ethylene glycol) divinyl ether
Triethylene glycol, anhydrous
112-27-6
97% by volume triethylene glycol, anhydrous,
75% by volume triethylene glycol, anhydrous, 100 mM NaCl; 10 mM Tris-Cl pH 7.5
Triethylene glycol monoethyl ether
112-50-5
90% by volume triethylene glycol monoethyl ether,
68% by volume triethylene glycol monoethyl ether, 100 mM NaCl; 10 mM Tris-Cl pH 7.5

TABLE 3

| The commercially available products of the Company QIAGEN used in the Examples | |
|---|---|
| MagAttract ® Suspension G | Suspension with magnetic particles |
| Buffer PE | Wash buffer with weak organic base |
| Buffer AE | Low salt buffer |
| Buffer EB | Aqueous elution buffer |
| Buffer TE | Elution buffer; 10 mM Tris-Cl, mM EDTH pH 8 |
| RNase-free Water | Ultrapure water |
| Buffer AL | Lysis buffer comprising guanidinium hydrochloride |
| Buffer RLT | Buffer comprising thiocyanate |
| Buffer ATL | Buffer comprising EDTA and SDS |
| Buffer ML | Buffer comprising guanidinium thiocyanate and t-octylphenoxy-polyoxy ethanol |
| Buffer AP1 | Buffer comprising EDTA and SDS |
| Buffer AW1 | Wash buffer comprising guanidinium hydrochloride |
| Buffer AW2 | Wash buffer comprising sodium azide |
| Buffer RW1 | Alcohol-containing buffer with guanidinium salt |
| Buffer RPE | Aqueous buffer |
| MTP-MP | Microtiter plate |

TABLE 3-continued

The commercially available products of the Company QIAGEN used in the Examples

| | |
|---|---|
| EMT | Elution microtubes |
| Buffer PM | Binding buffer comprising guanidinium chloride and 2-propanol |
| Buffer MW1 (comprises Ethanol) | Use buffer comprising guanidinium hydrochloride and ethanol |
| Buffer MW2 (comprises Ethanol) | Buffer with lithium chloride and ethanol |
| GTC | Guanidinium thiocyanate |
| MW1 Replacement Buffer (does not contain Ethanol) | Replacement buffer comprising guanidinium hydrochloride |
| MW2 Replacement Buffer (does not contain Ethanol) | Buffer with lithium chloride |
| RDD | RNAse-free buffer |
| AlAamp Spin | Buffer with lithium chloride and ethanol |
| K-AC | Potassium acetate |
| EGME | Ethylene glycol monomethyl ether |
| MagSep | Magnetic separation |
| MagStep | Step for magnetic separation |
| Buffer BL | Guanidinium thiocyanate-containing buffer |
| Buffer BW | Wash buffer for the effective desalination of DNA |
| Buffer BD | NaOH-containing buffer |

The invention claimed is:

1. A method for the washing of nucleic acids immobilized on one or more surfaces, wherein the nucleic acids are brought into contact with a wash buffer comprising less than 24% by volume of alcohol having 1 to 3 carbon atoms and at least one further solvent selected from the group consisting of alkane diols and alkane triols having 2 to 6 carbon atoms, monocarboxylic acid esters and dicarboxylic acid diesters having 2 to 6 carbon atoms in the acidic component and 1 to 4 carbon atoms in the alcoholic component; (poly)ethylene glycols and ether derivatives and ester derivatives thereof, with "poly" representing 2 to 200 repetitive ethylene glycol units, poly-(2-ethyl-2-oxazoline); and poly(4-styrene sulfonic acid-co-maleic acid) sodium salt solution.

2. The method for the washing of nucleic acids immobilized on one or more surfaces according to claim 1, wherein the wash buffer comprises one or more solvents selected from the group consisting of 1,2-butanediol, 1,2-propanediol, 1,3-butanediol, 1-methoxy-2-propanol acetate, 3-methyl-1,3,5-pentanetriol, DBE-2, DBE-3, DBE-4, DBE-5, DBE-6, diethylene glycol monoethyl ether (DGME), diethylene glycol monoethyl ether acetate (DGMEA), ethyl lactate, ethylene glycol, poly(2-ethyl-2-oxazoline), poly(4-styrene sulfonic acid-co-maleic acid) sodium salt solution, tetraethylene glycol (TEG), tetraglycol, tetrahydrofurfuryl polyethylene glycol 200, tri(ethylene glycol) divinyl ether, anhydrous triethylene glycol, and triethylene glycol monoethyl ether.

3. The method for the washing of nucleic acids immobilized on one or more surfaces according to claim 1, wherein the wash buffer comprises one or more solvents selected from the group consisting of tetraglycol, tetraethylene glycol, 1,3-butanediol, and 1,2-butanediol and triethylene glycol monoethyl ether.

4. The method according to claim 1, wherein the nucleic acid is genomic DNA.

5. The method according to claim 1, wherein the nucleic acid is total RNA.

6. The method according to claim 1, wherein the nucleic acids are short double-stranded DNA fragments.

7. The method of claim 1, wherein the surface is based on a material selected from the group consisting of: silica, a carboxylated surface, a zeolite, and titanium dioxide.

8. The method of claim 7, wherein the surface is a silica-based membrane or a silica-based magnetic particle.

9. A method for the extraction of nucleic acids from a solution, comprising the following steps:
    (a) adding a binding mediator to the nucleic-acid containing solution,
    (b) contacting the solution containing the binding mediator and the nucleic acids with a surface under chaotropic and/or high salt conditions,
    (c) binding or adsorption of the nucleic acids to a surface,
    (d) washing the surface according to a method of claim 1,
    (e) recovery of the nucleic acids adsorbed on the surface, by elution.

10. The method of claim 9, wherein the surface is based on a material selected from the group consisting of: silica, a carboxylated surface, a zeolite, and titanium dioxide.

11. The method of claim 10, wherein the surface is a silica-based membrane or a silica-based magnetic particle.

12. The method of claim 9, wherein the binding mediator is selected from the group consisting of diethylene glycol monoethyl ether, diethylene glycol monoethyl ether acetate, furfuryl alcohol, poly(1-vinylpyrrolidon-co-2-dimethyl-aminoethyl-methacrylate), poly(2-ethyl-2-oxazoline), poly(4-ammonium-styrene-sulfonic acid), tetraethylene glycol dimethyl ether, tetraethylene glycol, tetrahydrofurfuryl-polyethylene glycol 200 and triethylene glycol monoethyl ether.

13. A reagent kit for washing nucleic acids immobilized on one or more surfaces, comprising
    a solution 1 comprising a wash buffer comprising less than 24% by volume of alcohol having 1 to 3 carbon atoms and at least one further solvent selected from the group consisting of alkane diols and alkane triols having 2 to 6 carbon atoms, monocarboxylic acid esters and dicarboxylic acid diesters having 2 to 6 carbon atoms in the acidic component and 1 to 4 carbon atoms in the alcoholic component; (poly)ethylene glycols and ether derivatives and ester derivatives thereof, with "poly" representing 2 to 200 repetitive ethylene glycol units, poly-(2-ethyl-2-oxazoline); and poly(4-styrene sulfonic acid-co-maleic acid) sodium salt solution.

14. The reagent kit according to claim 13, further comprising
    a solution 2 comprising binding mediator, and
    a solution 3 comprising an eluant.

15. The reagent kit according to claim 14, further comprising a solution 4 comprising a lysis buffer and a protease.

16. The reagent kit of claim 14, wherein the binding mediator is selected from the group consisting of diethylene glycol monoethyl ether, diethylene glycol monoethyl ether acetate, furfuryl alcohol, poly(1-vinylpyrrolidon-co-2-dimethyl-aminoethyl-methacrylate), poly(2-ethyl-2-oxazoline), poly(4-ammonium-styrene-sulfonic acid), tetraethylene glycol dimethyl ether, tetraethylene glycol, tetrahydrofurfuryl-polyethylene glycol 200 and triethylene glycol monoethyl ether.

17. The reagent kit according to claim 13 for the extraction of nucleic acids from biological materials.

18. The reagent kit according to claim 17 for the purification of nucleic acids from biochemical reactions, PCR reactions and/or in vitro nucleic acid modification reactions.

19. The reagent kit of claim 16, wherein the biological material is selected from the group consisting of blood, tissue, smear preparations, bacteria, cell suspensions and adherent cells.

* * * * *